United States Patent
Miller et al.

(10) Patent No.: US 10,456,261 B2
(45) Date of Patent: Oct. 29, 2019

(54) DEVICES, SYSTEMS AND METHODS FOR MANUFACTURING ORTHOPEDIC IMPLANTS

(71) Applicant: ConforMIS, Inc., Bedford, MA (US)

(72) Inventors: Bob Miller, Secaucus, NJ (US); Ernest A. Dion, Danvers, MA (US); David P. Hesketh, Methuen, MA (US); Manuel J. Salinas, North Andover, MA (US); Philipp Lang, Lexington, MA (US)

(73) Assignee: ConforMIS, Inc., Billerica, MA (US)

(*) Notice: Subject to any disclaimer, the term of this patent is extended or adjusted under 35 U.S.C. 154(b) by 0 days.

(21) Appl. No.: 15/226,370

(22) Filed: Aug. 2, 2016

(65) Prior Publication Data
US 2017/0112626 A1    Apr. 27, 2017

Related U.S. Application Data

(62) Division of application No. 13/746,742, filed on Jan. 22, 2013, now Pat. No. 9,408,686.

(60) Provisional application No. 61/589,163, filed on Jan. 20, 2012.

(51) Int. Cl.
*A61F 2/30* (2006.01)
*B23P 17/00* (2006.01)

(52) U.S. Cl.
CPC .......... *A61F 2/30942* (2013.01); *B23P 17/00* (2013.01); *A61F 2/30* (2013.01); *A61F 2002/30317* (2013.01); *A61F 2002/30616* (2013.01); *A61F 2002/30952* (2013.01); *Y10T 29/49995* (2015.01); *Y10T 29/49996* (2015.01); *Y10T 29/49998* (2015.01)

(58) Field of Classification Search
CPC ........ A61F 2/30942; A61F 2002/30616; A61F 2002/30952; A61F 2/30; A61F 2002/30317; B23P 17/00; Y10T 29/49998; Y10T 29/49995; Y10T 29/49996
See application file for complete search history.

(56) References Cited

U.S. PATENT DOCUMENTS

| | | | |
|---|---|---|---|
| 4,673,409 A | 6/1987 | Van Kampen | |
| 4,822,365 A | 4/1989 | Walker et al. | |
| 4,841,975 A | 6/1989 | Woolson | |
| 4,936,862 A | 6/1990 | Walker et al. | |
| 5,007,936 A | 4/1991 | Woolson | |
| 5,067,964 A | 11/1991 | Richmond et al. | |
| 5,129,908 A | 7/1992 | Petersen | |

(Continued)

FOREIGN PATENT DOCUMENTS

| | | |
|---|---|---|
| CN | 1480111 A | 3/2004 |
| DE | 3933459 A1 | 4/1991 |

(Continued)

OTHER PUBLICATIONS

International Search Report—International Application No. PCT/US2013/035536 dated Jul. 18, 2013, together with the Written Opinion of the International Searching Authority, 9 pages.

(Continued)

*Primary Examiner* — John C Hong
(74) *Attorney, Agent, or Firm* — Sunstein Kann Murphy & Timbers LLP

(57) ABSTRACT

Methods, system, devices, processes and techniques are disclosed for manufacturing orthopedic implants utilizing blanks and/or fixtures.

7 Claims, 11 Drawing Sheets

(56) References Cited

U.S. PATENT DOCUMENTS

| | | |
|---|---|---|
| 5,246,530 A | 9/1993 | Bugle et al. |
| 5,274,565 A | 12/1993 | Reuben |
| 5,365,996 A | 11/1994 | Crook |
| 5,507,820 A | 4/1996 | Pappas |
| 5,682,886 A | 11/1997 | Delp et al. |
| 5,735,277 A | 4/1998 | Schuster |
| 5,741,215 A | 4/1998 | D'Urso |
| 5,768,134 A | 6/1998 | Swaelens et al. |
| 6,112,109 A | 8/2000 | D'Urso |
| 6,126,690 A | 10/2000 | Ateshian et al. |
| 6,161,080 A | 12/2000 | Aouni-Ateshian et al. |
| 6,205,411 B1 | 3/2001 | Digioia, III et al. |
| 6,206,927 B1 | 3/2001 | Fell et al. |
| 6,251,143 B1 | 6/2001 | Schwartz et al. |
| 6,254,639 B1 | 7/2001 | Peckitt |
| 6,280,478 B1 | 8/2001 | Richter et al. |
| 6,459,948 B1 | 10/2002 | Ateshian et al. |
| 6,510,334 B1 | 1/2003 | Schuster et al. |
| 6,540,786 B2 | 4/2003 | Chibrac et al. |
| 6,632,246 B1 | 10/2003 | Simon et al. |
| 6,677,554 B2 | 1/2004 | Darrah et al. |
| 6,679,917 B2 | 1/2004 | Ek |
| 6,694,207 B2 | 2/2004 | Darrah et al. |
| 6,712,856 B1 | 3/2004 | Carignan et al. |
| 6,799,066 B2 | 9/2004 | Steines et al. |
| 6,905,514 B2 | 6/2005 | Carignan et al. |
| 6,932,842 B1 | 8/2005 | Litschko et al. |
| 6,978,188 B1 | 12/2005 | Christensen |
| 7,001,672 B2 | 2/2006 | Justin et al. |
| 7,172,596 B2 | 2/2007 | Coon et al. |
| 7,239,908 B1 | 7/2007 | Alexander et al. |
| 7,368,065 B2 | 5/2008 | Yang et al. |
| 7,445,640 B2 | 11/2008 | Despres, III |
| 7,468,075 B2 | 12/2008 | Lang et al. |
| 7,603,192 B2 | 10/2009 | Martin et al. |
| 7,632,575 B2 | 12/2009 | Justin et al. |
| 7,718,109 B2 | 5/2010 | Robb et al. |
| 7,881,768 B2 | 2/2011 | Lang et al. |
| 7,983,777 B2 | 7/2011 | Melton et al. |
| 8,021,154 B2 | 9/2011 | Holzner et al. |
| 8,036,729 B2 | 10/2011 | Alexander et al. |
| 8,070,752 B2 | 12/2011 | Metzger et al. |
| 8,086,336 B2 | 12/2011 | Christensen |
| 8,092,462 B2 | 1/2012 | Pinczewski et al. |
| 8,112,142 B2 | 2/2012 | Alexander et al. |
| RE43,282 E | 3/2012 | Alexander et al. |
| 8,160,345 B2 | 4/2012 | Pavlovskaia et al. |
| 8,211,181 B2 | 7/2012 | Walker |
| 8,221,430 B2 | 7/2012 | Park et al. |
| 8,234,097 B2 | 7/2012 | Steines et al. |
| 8,282,646 B2 | 10/2012 | Schoenefeld et al. |
| 8,306,601 B2 | 11/2012 | Lang et al. |
| 8,311,306 B2 | 11/2012 | Pavlovskaia et al. |
| 8,337,507 B2 | 12/2012 | Lang et al. |
| 8,337,508 B2 | 12/2012 | Lavallee et al. |
| 8,343,218 B2 | 1/2013 | Lang et al. |
| 8,352,056 B2 | 1/2013 | Lee et al. |
| 8,357,166 B2 | 1/2013 | Aram et al. |
| 8,369,926 B2 | 2/2013 | Lang et al. |
| 8,377,066 B2 | 2/2013 | Katrana et al. |
| 8,377,068 B2 | 2/2013 | Aker et al. |
| 8,377,073 B2 | 2/2013 | Wasielewski |
| 8,380,471 B2 | 2/2013 | Iannotti et al. |
| 8,398,646 B2 | 3/2013 | Metzger et al. |
| 8,407,067 B2 | 3/2013 | Uthgenannt et al. |
| 8,419,740 B2 | 4/2013 | Aram et al. |
| 8,425,524 B2 | 4/2013 | Aker et al. |
| 8,457,930 B2 | 6/2013 | Schroeder |
| 8,473,305 B2 | 6/2013 | Belcher et al. |
| 8,480,754 B2 | 7/2013 | Bojarski et al. |
| 8,486,150 B2 | 7/2013 | White et al. |
| 8,532,807 B2 | 9/2013 | Metzger |
| 8,545,569 B2 | 10/2013 | Fitz et al. |
| 8,556,983 B2 | 10/2013 | Bojarski et al. |
| 8,617,242 B2 | 12/2013 | Philipp |
| 8,634,617 B2 | 1/2014 | Tsougarakis et al. |
| 8,638,998 B2 | 1/2014 | Steines et al. |
| 8,690,945 B2 | 4/2014 | Fitz et al. |
| 8,709,089 B2 | 4/2014 | Lang et al. |
| 8,735,773 B2 | 5/2014 | Lang |
| 8,768,028 B2 | 7/2014 | Lang et al. |
| 8,771,365 B2 | 7/2014 | Bojarski et al. |
| 8,801,720 B2 | 8/2014 | Park et al. |
| 8,906,107 B2 | 12/2014 | Bojarski et al. |
| 9,020,788 B2 | 4/2015 | Bojarski et al. |
| 9,180,015 B2 | 11/2015 | Fitz et al. |
| 9,186,254 B2 | 11/2015 | Fitz et al. |
| 9,308,091 B2 | 4/2016 | Lang et al. |
| 9,333,085 B2 | 5/2016 | Fitz et al. |
| 9,387,083 B2 | 7/2016 | Al et al. |
| 9,408,686 B1 | 8/2016 | Miller et al. |
| 9,439,767 B2 | 9/2016 | Bojarski et al. |
| 9,517,134 B2 | 12/2016 | Lang et al. |
| 9,579,110 B2 | 2/2017 | Bojarski et al. |
| 9,603,711 B2 | 3/2017 | Bojarski et al. |
| 9,636,229 B2 | 5/2017 | Lang et al. |
| 9,700,420 B2 | 7/2017 | Fitz et al. |
| 9,700,971 B2 | 7/2017 | Lang et al. |
| 9,737,367 B2 | 8/2017 | Steines et al. |
| 9,775,680 B2 | 10/2017 | Bojarski et al. |
| 9,849,019 B2 | 12/2017 | Miller et al. |
| 9,872,773 B2 | 1/2018 | Lang et al. |
| 9,877,790 B2 | 1/2018 | Bojarski et al. |
| 9,913,723 B2 | 3/2018 | Fitz et al. |
| 9,943,370 B2 | 4/2018 | Asseln et al. |
| 2002/0028980 A1 | 3/2002 | Thierfelder et al. |
| 2002/0052606 A1 | 5/2002 | Bonutti |
| 2002/0059049 A1 | 5/2002 | Bradbury et al. |
| 2002/0072821 A1 | 6/2002 | Baker |
| 2002/0079601 A1 | 6/2002 | Russell et al. |
| 2002/0082741 A1 | 6/2002 | Mazumder et al. |
| 2002/0087274 A1 | 7/2002 | Alexander et al. |
| 2002/0127264 A1 | 9/2002 | Felt et al. |
| 2003/0055502 A1 | 3/2003 | Lang et al. |
| 2003/0080957 A1 | 5/2003 | Stewart et al. |
| 2003/0236473 A1 | 12/2003 | Dore et al. |
| 2004/0098133 A1 | 5/2004 | Carignan et al. |
| 2004/0102866 A1 | 5/2004 | Harris et al. |
| 2004/0117015 A1 | 6/2004 | Biscup |
| 2005/0119664 A1 | 6/2005 | Carignan et al. |
| 2005/0137601 A1 | 6/2005 | Assell et al. |
| 2005/0148843 A1 | 7/2005 | Roose et al. |
| 2005/0154471 A1 | 7/2005 | Aram et al. |
| 2005/0197814 A1 | 9/2005 | Aram et al. |
| 2005/0216305 A1 | 9/2005 | Funderud |
| 2005/0244239 A1 | 11/2005 | Shimp |
| 2005/0267584 A1 | 12/2005 | Burdulis, Jr. et al. |
| 2006/0069318 A1 | 3/2006 | Keaveny et al. |
| 2006/0094951 A1 | 5/2006 | Dean et al. |
| 2006/0136058 A1 | 6/2006 | Pietrzak |
| 2006/0149283 A1 | 7/2006 | May et al. |
| 2006/0241776 A1 | 10/2006 | Brown et al. |
| 2007/0005143 A1 | 1/2007 | Ek et al. |
| 2007/0118055 A1 | 5/2007 | McCombs |
| 2007/0118243 A1 | 5/2007 | Schroeder et al. |
| 2007/0142914 A1 | 6/2007 | Jones et al. |
| 2007/0198022 A1 | 8/2007 | Lang et al. |
| 2007/0226986 A1 | 10/2007 | Park et al. |
| 2007/0233141 A1 | 10/2007 | Park et al. |
| 2007/0255288 A1 | 11/2007 | Mahfouz et al. |
| 2007/0276501 A1 | 11/2007 | Betz et al. |
| 2007/0288030 A1 | 12/2007 | Metzger et al. |
| 2008/0004709 A1 | 1/2008 | O'Neill et al. |
| 2008/0058945 A1 | 3/2008 | Hajaj et al. |
| 2008/0114370 A1 | 5/2008 | Schoenefeld et al. |
| 2008/0147072 A1 | 6/2008 | Park et al. |
| 2008/0172125 A1 | 7/2008 | Ek |
| 2008/0195216 A1 | 8/2008 | Philipp |
| 2008/0215059 A1 | 9/2008 | Carignan et al. |
| 2008/0257363 A1 | 10/2008 | Schoenefeld et al. |
| 2008/0262624 A1 | 10/2008 | White et al. |
| 2009/0072447 A1 | 3/2009 | Hull et al. |
| 2009/0088753 A1 | 4/2009 | Aram et al. |
| 2009/0099567 A1 | 4/2009 | Zajac |

(56) References Cited

U.S. PATENT DOCUMENTS

| | | | |
|---|---|---|---|
| 2009/0110498 A1* | 4/2009 | Park | A61B 17/15 408/1 R |
| 2009/0131941 A1 | 5/2009 | Park et al. | |
| 2009/0138020 A1 | 5/2009 | Park et al. | |
| 2009/0149977 A1 | 6/2009 | Schendel | |
| 2009/0151736 A1 | 6/2009 | Belcher et al. | |
| 2009/0226068 A1 | 9/2009 | Fitz et al. | |
| 2009/0270868 A1 | 10/2009 | Park et al. | |
| 2010/0049195 A1 | 2/2010 | Park et al. | |
| 2010/0082035 A1 | 4/2010 | Keefer | |
| 2010/0087829 A1 | 4/2010 | Metzger et al. | |
| 2010/0152741 A1 | 6/2010 | Park et al. | |
| 2010/0217270 A1 | 8/2010 | Polinski et al. | |
| 2010/0256479 A1 | 10/2010 | Park et al. | |
| 2010/0292963 A1 | 11/2010 | Schroeder | |
| 2010/0303313 A1 | 12/2010 | Lang et al. | |
| 2010/0332194 A1 | 12/2010 | McGuan et al. | |
| 2011/0029091 A1 | 2/2011 | Bojarski et al. | |
| 2011/0029093 A1 | 2/2011 | Bojarski et al. | |
| 2011/0046735 A1 | 2/2011 | Metzger et al. | |
| 2011/0071533 A1 | 3/2011 | Metzger et al. | |
| 2011/0087332 A1 | 4/2011 | Bojarski et al. | |
| 2011/0087465 A1 | 4/2011 | Mahfouz | |
| 2011/0092804 A1 | 4/2011 | Schoenefeld et al. | |
| 2011/0093108 A1 | 4/2011 | Ashby et al. | |
| 2011/0112808 A1 | 5/2011 | Anderson et al. | |
| 2011/0184526 A1 | 7/2011 | White et al. | |
| 2011/0218545 A1 | 9/2011 | Catanzarite et al. | |
| 2011/0264097 A1 | 10/2011 | Hodorek et al. | |
| 2011/0266265 A1 | 11/2011 | Lang | |
| 2011/0305379 A1 | 12/2011 | Mahfouz | |
| 2012/0022659 A1 | 1/2012 | Wentorf et al. | |
| 2012/0078598 A1 | 3/2012 | McDaniel | |
| 2012/0116203 A1 | 5/2012 | Vancraen et al. | |
| 2012/0141034 A1 | 6/2012 | Iannotti et al. | |
| 2012/0209394 A1 | 8/2012 | Bojarski et al. | |
| 2012/0239045 A1 | 9/2012 | Li | |
| 2012/0265496 A1 | 10/2012 | Mahfouz | |
| 2012/0276509 A1 | 11/2012 | Iannotti et al. | |
| 2012/0310364 A1 | 12/2012 | Li et al. | |
| 2012/0316564 A1 | 12/2012 | Serbousek et al. | |
| 2012/0323246 A1 | 12/2012 | Catanzarite et al. | |
| 2013/0006250 A1 | 1/2013 | Metzger et al. | |
| 2013/0035766 A1 | 2/2013 | Meridew | |
| 2013/0066321 A1 | 3/2013 | Mannss et al. | |
| 2013/0119579 A1 | 5/2013 | Iannotti et al. | |
| 2013/0158671 A1 | 6/2013 | Uthgenannt et al. | |
| 2013/0199259 A1 | 8/2013 | Smith | |
| 2013/0203031 A1 | 8/2013 | McKinnon et al. | |
| 2013/0211242 A1 | 8/2013 | Bertrand et al. | |
| 2013/0220570 A1 | 8/2013 | Sears et al. | |
| 2013/0245803 A1 | 9/2013 | Lang | |
| 2013/0253522 A1 | 9/2013 | Bojarski et al. | |
| 2014/0039631 A1 | 2/2014 | Bojarski et al. | |
| 2014/0065194 A1 | 3/2014 | Yoo et al. | |
| 2014/0086780 A1 | 3/2014 | Miller et al. | |
| 2014/0109384 A1 | 4/2014 | Lang | |
| 2014/0172111 A1 | 6/2014 | Lang et al. | |
| 2014/0222157 A1 | 8/2014 | Al et al. | |
| 2014/0222390 A1 | 8/2014 | Asseln et al. | |
| 2014/0250677 A1 | 9/2014 | Lang | |
| 2014/0257508 A1 | 9/2014 | Bojarski et al. | |
| 2014/0259629 A1 | 9/2014 | Dion et al. | |
| 2014/0324205 A1 | 10/2014 | Park et al. | |
| 2015/0081029 A1 | 3/2015 | Bojarski et al. | |
| 2015/0093283 A1 | 4/2015 | Miller et al. | |
| 2016/0045317 A1 | 2/2016 | Lang et al. | |
| 2017/0112626 A1 | 4/2017 | Miller et al. | |
| 2017/0119531 A1 | 5/2017 | Bojarski et al. | |
| 2017/0164957 A1 | 6/2017 | Bojarski et al. | |
| 2017/0231783 A1 | 8/2017 | Lang et al. | |
| 2017/0296349 A1 | 10/2017 | Slamin et al. | |
| 2017/0360567 A1 | 12/2017 | Fitz et al. | |
| 2017/0367834 A1 | 12/2017 | Fitz et al. | |
| 2018/0008417 A1 | 1/2018 | Lang | |

FOREIGN PATENT DOCUMENTS

| | | |
|---|---|---|
| DE | 4434539 C2 | 6/1998 |
| DE | 10055465 A1 | 5/2002 |
| DE | 102006037067 B4 | 6/2011 |
| EP | 0704193 A1 | 4/1996 |
| EP | 1074229 B1 | 10/2005 |
| EP | 1683593 A2 | 7/2006 |
| EP | 2173260 B1 | 1/2012 |
| JP | H07236648 A | 9/1995 |
| JP | H0825487 A | 1/1996 |
| JP | H09169056 A | 6/1997 |
| JP | 2001502565 | 2/2001 |
| JP | 200285435 | 3/2002 |
| JP | 2004166802 A | 6/2004 |
| JP | 2005532089 A | 10/2005 |
| JP | 2007236926 A | 9/2007 |
| JP | 2010538882 A | 12/2010 |
| WO | WO-9325157 A1 | 12/1993 |
| WO | WO-9528688 A1 | 10/1995 |
| WO | WO-9814128 A1 | 4/1998 |
| WO | WO-0035346 A2 | 6/2000 |
| WO | WO-0059411 A1 | 10/2000 |
| WO | WO-0068749 A1 | 11/2000 |
| WO | WO-0166021 A1 | 9/2001 |
| WO | WO-0170142 A1 | 9/2001 |
| WO | WO-0177988 A2 | 10/2001 |
| WO | WO-0222013 A1 | 3/2002 |
| WO | WO-0222014 A1 | 3/2002 |
| WO | WO-03094782 A2 | 11/2003 |
| WO | WO-2004047688 A1 | 6/2004 |
| WO | WO-2005002473 A1 | 1/2005 |
| WO | WO-2006092600 A1 | 9/2006 |
| WO | WO-2008021494 A2 | 2/2008 |
| WO | WO-2008101090 A2 | 8/2008 |
| WO | WO-2009001083 A1 | 12/2008 |
| WO | WO-2009039159 A2 | 3/2009 |
| WO | WO-2009068892 A1 | 6/2009 |
| WO | WO-2009106366 A1 | 9/2009 |
| WO | WO-2009106816 A1 | 9/2009 |
| WO | WO-2010099353 A1 | 9/2010 |
| WO | WO-2010099359 A1 | 9/2010 |
| WO | WO-2010148103 A1 | 12/2010 |
| WO | WO-2011028624 A1 | 3/2011 |
| WO | WO-2011056995 A2 | 5/2011 |
| WO | WO-2011059641 A1 | 5/2011 |
| WO | WO-2011094540 A2 | 8/2011 |
| WO | WO-2011101474 A1 | 8/2011 |
| WO | WO-2011109260 A1 | 9/2011 |
| WO | WO-2011130421 A1 | 10/2011 |
| WO | WO-2012021241 A2 | 2/2012 |
| WO | WO-2012021846 A2 | 2/2012 |
| WO | WO-2012021894 A2 | 2/2012 |
| WO | WO-2012021895 A2 | 2/2012 |
| WO | WO-2012027150 A2 | 3/2012 |
| WO | WO-2012051542 A2 | 4/2012 |
| WO | WO-2012112698 A2 | 8/2012 |
| WO | WO-2013062850 A1 | 5/2013 |
| WO | WO-2013152341 A1 | 10/2013 |
| WO | WO-2013155500 A1 | 10/2013 |
| WO | WO-2014047514 A1 | 3/2014 |
| WO | WO-2014145267 A1 | 9/2014 |

OTHER PUBLICATIONS

Invitation to Pay Additional Fees—International Application No. PCT/US2008/053977, dated Jul. 11, 2008, together with the Written Opinion of the International Searching Authority, 6 pages.
"Office Action pertaining to JP Application No. 2012-109834, dated Jun. 24, 2016, English translation attached, 11 pages.".
Partial Supplementary European Search Report—Application No. 13771863.1-1654, dated Apr. 26, 2016, 7 pages.
Birnbaum et al. "Computer-Assisted Orthopedic Surgery With Individual Templates and Comparison to Conventional Operation Method", Spine, vol. 26, No. 4, pp. 365-369, Feb. 2001.
Blazina MD et al. Patellofemoral Replacement: Utilizing a customized Femoral Groove Replacement Techniques Orthop 5(1):53-55 (1990).

(56) References Cited

OTHER PUBLICATIONS

Brandt et al. "CRIGOS—Development of a Compact Robot System for Image-Guided Orthopedic Surgery," Der Orthopäde, Springer-Verlag, vol. 29, No. 7, pp. 645-649 (Jul. 2000) (English Translation with Certification).

Brandt et al. "CRIGOS—Development of a Compact Robot System for Image-Guided Orthopedic Surgery," Der Orthopäde, Springer-Verlag, vol. 29, No. 7, pp. 645-649 (Jul. 2000) (In German).

Chelule et al. "Computer Aided Design of Personalized Jigs in Total Knee Replacement", 3rd Annual Meeting of CAOS Int'l Proc., Spain, Jun. 18, 21, 2003, pp. 58-59.

Chelule et al. "Patient-Specific Template to Preserve Bone Stock in Total Knee Replacement: Preliminary Results", 15th Annual ISTA Symposium, Sep. 2002, 1 page.

Cohen et al. "Computer-Aided Planning of Patellofemoral Joint OA Surgery: Developing Physical Models from Patient MRI", MICCAI, Oct. 11-13, 1998, 13 pages.

Cohen et al. "Knee Cartilage Topography Thickness and Contact Areas From MRI: In-Vitro Calibration and In-Vivo Measurements", Osteoarthritis and Cartilage vol. 7, No. 1, pp. 95-109 (1999).

Delp et al. A Graphics-Based Software System to Develop and Analyze Models of Musculoskeletal Structures, Comput. Biol. Med., vol. 25, No. 1, pp. 21-34, 1995.

Delp et al. "Computer Assisted Knee Replacement", Clinical Orthopaedics, pp. 49-56, Sep. 1998.

Extended European Search Report—Application No. 12192903.8-1654 dated Apr. 17, 2013, 8 pages.

Extended European Search Report—Application No. 13775348.9-1654 dated Mar. 10, 2015, 6 pages.

Froemel et al. "Computer Assisted Template Based Navigation for Total Knee Replacement", Documents presented at CAOS on Jun. 17, 2001, 4 pages.

Hafez et al. "Computer Assisted Total Knee Replacement: Could a Two-Piece Custom Template Replace the Complex Conventional Instrumentations?", 4th Annual Meeting of CAOS Int'l Proc., Chicago, Jun. 16-19, 2004, pp. 63-64.

Hafez et al. "Computer Assisted Total Knee Replacement: Could a Two-Piece Custom Template Replace the Complex Conventional Instrumentations?" Session 6: Novel Instruments; Computer Aided Surgery, Session 6, vol. 9, No. 3, pp. 93-94 (Jun. 2004).

Hafez et al. "Computer-Assisted Total Hip Arthroplasty: The Present and the Future", Future Rheumatol., vol. 1, pp. 121-131, 2006.

Hafez et al. "Computer-assisted Total Knee Arthroplasty Using Patient-specific Templating," Clinical Orthopaedics and Related Research, No. 444, pp. 184-192 (Mar. 2006).

Harrysson et al.—"Custom-Designed Orthopedic Implants Evaluated Using Finite Element Analysis of Patient-Specific Computed Tomography Data: Femoral-Component Case Study", BMC Musculoskeletal Disorders, vol. 8(91), Sep. 2007, 10 pages.

International Search Report—International Application No. PCT/US2008/053977, dated Sep. 30, 2008, together with the Written Opinion of the International Searching Authority, 17 pages.

International Search Report—International Application No. PCT/US2012/025274 dated Oct. 25, 2012, together with the Written Opinion of the International Searching Authority, 12 pages.

International Search Report—International Application No. PCT/US2013/036505 dated Jul. 29, 2013, together with the Written Opinion of the International Searching Authority, 7 pages.

International Search Report—International Application No. PCT/US2013/061042 dated Jan. 10, 2014, together with the Written Opinion of the International Searching Authority, 12 pages.

International Search Report—International Application No. PCT/US2014/030001 dated Aug. 27, 2014, together with the Written Opinion of the International Searching Authority, 10 pages.

Kidder J. et al.3D Model Acquisition Design Planning and Manufacturing of Orthopaedic Devices: A Framework Proceedings of the SPIE Advanced Sensor and Control-System Interface Boston MA vol. 2911 pp. 9-22 21 (Nov. 1996).

Lombardi, Jr. et al. "Patient-Specific Approach in Total Knee Arthroplasty", Orthopedics, vol. 31, Issue 9, Sep. 2008, 8 pages.

Mumtaz et al. "Selective Laser Melting of Inconel 625 Using Pulse Shaping", Rapid Prototyping Journal, ® vol. 16, Iss. 4, pp. 248-257, 2010.

Office Action dated Dec. 1, 2015, pertaining to U.S. Appl. No. 14/033,350, 8 pages.

Office Action dated Feb. 19, 2016, pertaining to U.S. Appl. No. 14/285,151, 7 pages.

Office Action dated Nov. 19, 2015, pertaining to U.S. Appl. No. 14/033,095, 8 pages.

Office Action dated Nov. 27, 2015, pertaining to U.S. Appl. No. 14/134,064, 10 pages.

"Office Action pertaining to Japanese Patent Application No. 2015-505970 dated Nov. 24, 2015, 2 pages ( In Japanese)".

"Office Action pertaining to Japanese Patent Application No. 2015-505970 dated Nov. 24, 2015, 4 pages (English translation)".

Petrovic et al. "Additive Manufacturing Solutions for Improved Medical Implants", Biomedicine, INTECH, pp. 148-180, Mar. 2012.

Portheine et al. "Computer-Assisted Total Knee Endoprosthetics with Planning-Specific Treatment Templates", Biomed. Tech., vol. 46, Supp. vol. 1, Jan. 2001—English translation.

Portheine et al. "Computer-Assisted Total Knee Endoprosthetics with Planning-Specific Treatment Templates", Biomed. Tech., vol. 46, Supp. vol. 1, Jan. 2001—In German.

Portheine et al CT-Based Planning and Individual Template Navigation in TKA Navigation and Robotics in Total Joint and Spine Surgery Springer 48:336-342 (2004).

Portheine ET AL. Development of a clinical demonstrator for computer assisted orthopedic surgery with CT-image based individual templates Computer Assisted Radiology and Surgery (1997).

Portheine et al. "Potentials of CT-based Planning and Template-based Procedure in Hip and Knee Surgery", Orth. Prac., vol. 36, pp. 786-791, 2000—English Translation.

Portheine et al. "Potentials of CT-based Planning and Template-based Procedure in Hip and Knee Surgery", Orth. Prac., vol. 36, pp. 786-791, 2000—In German.

Portheine thesis : "Model-Based Operation Planning in Orthopedic Surgery", Thesis, RWTH Aachen University, Apr. 22, 2004, 90 pages—In German.

Portheine thesis "Model-Based Operation Planning in Orthopedic Surgery", Thesis, RWTH Aachen University, Apr. 22, 2004, 170 pages—English Translation.

Radermacher "Computer Assisted Matching of Planning and Execution in Orthopedic Surgery", Slide Presentation, San Diego, Nov. 29, 1993, 22 pages.

Radermacher "Computer-Based Decision Support in the Selection and Evaluation of Contact Surfaces for Manual Referencing", Lecture presented at Helmholtz Meeting '98 and OSS '98, 6 pages (1998)—® In German.

Radermacher "Computer-Based Decision Support in the Selection and Evaluation of Contact Surfaces for Manual Referencing", Lecture presented at Helmholtz Meeting '98 and OSS '98, 8 pages (1998)—English Translation.

Radermacher et al. Image Guided Orthopedic Surgery Using Individual Templates Experimental Results and Aspects of the Development of a Demonstrator for Pelvis Surgery in Troccaz J. Grimson E., Mosges R (eds). Computer Vision, Virtual Reality and Robotics in Medicine and Medical Robotics and Computer Assisted Surgery, Lecture Notes in Computer Science. Berlin, Springer-Verlag 606-616, 1997.

Radermacher et al. "Computer Assisted Matching of Planning and Execution in Orthopedic Surgery", IEEE, EMBS, San Diego, 1993, pp. 946-947.

Radermacher et al. "Computer Assisted Orthopedic Surgery by Means of Individual Templates •Aspects and Analysis of Potential Applications •" Proceedings of the First International Symposium on Medical Robotics and Computer Assisted Surgery, vol. 1: Sessions I-III, MRCAS '94, Pittsburgh, PA, pp. 42-48 (Sep. 22-24, 1994).

Radermacher et al. "Computer Based Decision Support for the Planning of Contact Faces for Manual Registration with Individual Templates", Helmholtz-Institute for Biomed. Eng., 7 pages, 1997-98.

(56) References Cited

OTHER PUBLICATIONS

Radermacher et al. "Computer Integrated Advanced Orthopedics (CIAO)", 2nd European Conference on Eng. and Med., presented Apr. 26, 1993, 12 pages.
Radermacher et al. "Computer Integrated Surgery—Connecting Planning and Execution of Surgical Intervention in Orthopedics", Surgical Therapy Technology, Helmholtz-Institut Aachen Research Report, 1991-1992, pp. 187, 196-202.
Radermacher et al. "Computer-assisted operative interventions in orthopedics—are there prospects for endoprosthetics as well?", Prac. Ortho., vol. 27, pp. 1-17, 1997—English Translation.
Radermacher et al. "Computer-assisted operative interventions in orthopedics—are there prospects for endoprosthetics as well?", Prac. Ortho., vol. 27, pp. 149-164, 1997—In German.
Radermacher et al. "Computer-Assisted Planning and Operation in Orthopedics", Orth. Prac. 36th year, pp. 731-737, Dec. 2000—English Translation.
Radermacher et al. "Computer-Assisted Planning and Operation in Orthopedics", Orth. Prac. 36th year, pp. 731-737, Dec. 2000—In German.
Radermacher, et al. CT Image Based Planning and Execution of Interventions in Orthopedic Surgery Using Individual Templates Experimental Results and Aspects of Clinical Applications. In Nolte LP, Ganz, R. (eds). CAOS Computer Assisted Orthopaedic Surgery. Bern, Hans Huber (In Press) 1998.
Radermacher et al. Technique for Better Execution of CT Scan Planned Orthopedic Surgery on Bone Structures. In Lemke HW Inamura K. Jaffe CC Vannier MW (eds). Computer Assisted Radiology Berlin Springer 933-938 1995.
Radermacher et al. "Surgical Therapy Technology", Helmholtz-Institut Aachen Research Report, 1993-1994, pp. 189-219.
Radermacher "Image Guided Orthopedic Surgery with Individual Templates", Helmhotz-Institute for Biomed. Eng., 2 pages, 1997.
Radermacher K. et al. Computer Integrated Orthopedic Surgery Connection of Planning and Execution in Surgical Inventions. In Taylor R. Lavallee S. Burdea G. Mosges R. (eds). Computer Integrated Surgery. Cambridge MIT press 451-463 1996.
Radermacher Klaus Computer Assisted Orthopaedic Surgery With Image Based Individual Templates Clinical Orthopaedics Sep. 1998 vol. 354 pp. 28-38.
Radermacher Klaus English Translation: Helmholtz Institute of Biomedical Technology Computer-Assisted Planning and Execution of Orthopedic Surgery Using Individual Surgical Templates May 18, 1999.
Radermacher Klaus German Version: Helmholtz Institute of Biomedical Technology Computer-Assisted Planning and Execution of Orthopedic Surgery Using Individual Surgical Templates May 18, 1999.
Radermacher "Template Based Navigation—An Efficient Technique for Hip and Knee Surgery", CAOS First Asian Meet, India, Mar. 27-28, 2004, pp. 44-50.
Rau et al. "Small and Neat", Medical Tech. Int'l, pp. 65, 67 and 69, 1993-94.
Schiffers et al. "Planning and execution of orthopedic surgery using individualized templates," Der Orthopäde, Springer-Verlag, vol. 29, No. 7, pp. 636-640, (Jul. 2000) (In German).
Schiffers et al. "Planning and execution of orthopedic surgery using individualized templates," Der Orthopäde, Springer-Verlag, vol. 29, No. 7, pp. 636-640, (Jul. 2000) (English Translation with Certification).
Schkommodau et al. "Clinical Application of Individual Templates for Pedicle Screw Placement in Comparison to Computer Navigation", Poster presented at CAOS, Feb. 18, 2000, 1 page.
Schkommodau et al. "Clinical Experience With the Individual Template Technique", Orth. Prac., vol. 37, No. 1, pp. 19-22, 2001—English Translation.
Schkommodau et al. "Clinical Experience With the Individual Template Technique", Orth. Prac., vol. 37, No. 1, pp. 19-22, 2001—In German.
Seel et al. "Three-Dimensional Planning and Virtual Radiographs in Revision Total Hip Arthroplasty for Instability", Clinical Orthopaedics and Related Research, No. 442, pp. 35-38, Jan. 2006.
Staudte et al. "Computer-Assisted Operation Planning and Technique in Orthopedics", North Rhine-Westphalia Acad. for Sciences, Lecture N.444, ISSN 0944-8799, 2000, 17 pages—In German.
Staudte et al. "Computer-Assisted Operation Planning and Technique in Orthopedics", North Rhine-Westphalia Acad. for Sciences, Lecture N.444, ISSN 0944-8799, 2000, 34 pages—English Translation.
Surgicad Design Combines 3-D Visualization with CAD Tools, Intergraph Corp. and Surgicad Corp. News Brief, 2 pages, Sep. 1993.
Thoma et al. "Custom-made knee endoprosthetics using subtraction data of three-dimensional CT scans—A new approach," Der Orthopäde, Springer-Verlag, vol. 29, No. 7, pp. 641-644, (Jul. 2000) (In German).
Thoma et al. "Custom-made knee endoprosthetics using subtraction data of three-dimensional CT scans—A new approach," Der Orthopäde, Springer-Verlag, vol. 29, No. 7, pp. 641-644, (Jul. 2000)(English Translation with Certification).
Thoma et al. "Use of a New Subtraction Procedure Based on Three-Dimensional CT Scans for the Individual Treatment of Bone Defects in the Hip and Knee," Journal DGPW, No. 17, pp. 27-28 (May 1999) (In German).
Thoma et al. "Use of a New Subtraction Procedure Based on Three-Dimensional CT Scans for the Individual Treatment of Bone Defects in the Hip and Knee," Journal DGPW, No. 17, pp. 27-28 (May 1999)(English Translation with Certification).
Wu et al. "Application of Laser Measuring, Numerical Simulation and Rapid Prototyping to Titanium Dental Castings", Dental Materials, vol. 17, pp. 102-108, 2001.

\* cited by examiner

DEVICES, SYSTEMS AND METHODS FOR MANUFACTURING ORTHOPEDIC IMPLANTS

RELATED APPLICATIONS

This application is a divisional of U.S. patent application Ser. No. 13/746,742, entitled "Devices, Systems and Methods for Manufacturing Orthopedic Implants," filed Jan. 22, 2013, which in turn claims the benefit of U.S. Provisional Application Ser. No. 61/589,163, entitled "Systems and Methods for Manufacturing, Preparation and Use of Blanks in Orthopedic Implants," filed Jan. 20, 2012. Each of the applications is hereby incorporated herein by reference in its entirety.

TECHNICAL FIELD

This application relates to devices, systems, methods, techniques and processes for manufacturing orthopedic implants, including the use of blanks and/or fixtures in such manufacturing.

BACKGROUND

Historically, diseased, injured or defective joints, such as, for example, joints exhibiting osteoarthritis, were repaired using standard off-the-shelf implants and other surgical devices. Surgical implant systems that employed a one-size-fits-all approach to implant design (and even those that utilized a "few-sizes-fit-all" approach, including modularly assembled systems) did not typically require highly accurate information about the patient's anatomy. Instead, such systems utilized gross anatomical measurements such as the maximum bone dimensions at the implant site, as well as the patient weight and age, to determine a "suitable" implant. The surgical procedure then concentrated on altering the underlying bony anatomical support structures (i.e., by cutting, drilling and/or otherwise modifying the bone structures) to accommodate the existing contact surfaces of the pre-manufactured implant. With these systems, varying quantities of implants and/or implant components would be manufactured and stockpiled. Once a potential patient was identified, an appropriate implant and/or component would be selected, transported to the surgical location and utilized in the patient's surgical procedure.

More recently, the joint replacement field has come to embrace the concept of "patient-adapted" (e.g., "patient-specific" and "patient-engineered") implant systems. With such systems, the surgical implants, associated surgical tools and procedures are designed or otherwise modified to account for and accommodate the individual anatomy of the patient undergoing the surgical procedure. Such systems typically utilize non-invasive imaging data, taken of the individual pre-operatively, to guide the design and/or selection of the implant, surgical tools, and the planning of the surgical procedure itself. Various objectives of these newer systems can include (1) reducing the amount of bony anatomy removed to accommodate the implant, (2) designing/selecting an implant that replicates and/or improves the function of the natural joint, (3) increasing the durability and functional lifetime of the implant, (4) simplifying the surgical procedure for the surgeon, (5) reducing patient recovery time and/or discomfort, and (6) improving patient outcomes.

Because patient-adapted implant systems are created using anatomical information from a particular patient, such systems are generally created after the patient has been designated a "surgical candidate" and undergone non-invasive imaging. But, because such systems are not generally pre-manufactured and stockpiled (as are traditional systems), there can be a considerable delay between patient diagnosis and the actual surgery, much of which is due to the amount of time necessary to design and manufacture the patient-adapted implant components using the patient image data.

A significant portion of any delay between patient diagnosis/imaging and actual surgery can often be attributed to the time needed to manufacture each patient-adapted implant system to a particular patient's anatomy. Often, such implants are manufactured individually or in small batches, using a 3rd party vendor, which can greatly increase the cost of creating such implant components as compared to the large batch manufacturing used with traditional non-custom implants.

In addition, because patient-adapted implant systems are manufactured in limited quantities, a fracture, failure or sufficient discrepancy identified at any point in the manufacturing process can have significant consequences, including the non-availability of implant components when needed and/or a requirement to remanufacture implant components and/or ordering implants on an expedited (and much more expensive) basis to meet deadlines.

Accordingly, there is a need in the art for advanced methods, techniques, devices and systems to ensure the availability of patient-adapted implant components for a scheduled surgery in a cost effective and efficient manner.

SUMMARY

This section provides a general summary of the disclosure and is not a comprehensive disclosure of its full scope or all of its features.

A method of manufacturing a surgical implant for treating a joint of a patient can include utilizing a blank. At least a portion of a bone-facing surface of the blank may be engaged with an engagement portion of an outer surface of a fixture, and the blank may be machined to form a joint-facing surface. The joint-facing surface of the blank may have a patient-adapted curvature in a first plane.

A fixture for use in manufacturing a surgical implant for treating a portion of a bone of a patient can include an outer surface. The outer surface may include an engagement portion configured to engage a portion of the implant in a known orientation during at least a portion of manufacturing the implant. The outer surface of the fixture may also include a connecting portion, which may be configured for releasably connecting to a processing apparatus in a predetermined orientation.

A blank for use in manufacturing a surgical implant can have a shape based, at least in part, on one or more features common to a class of patient-adapted implants. The blank can also include dimensions that are equal to or larger than corresponding dimensions of each patient-adapted implant included in the class of patient-adapted implants.

BRIEF DESCRIPTION OF THE DRAWINGS

The foregoing and other objects, aspects, features, and advantages of embodiments will become more apparent and may be better understood by referring to the following description, taken in conjunction with the accompanying drawings, in which.

DETAILED DESCRIPTION

Figure 1:
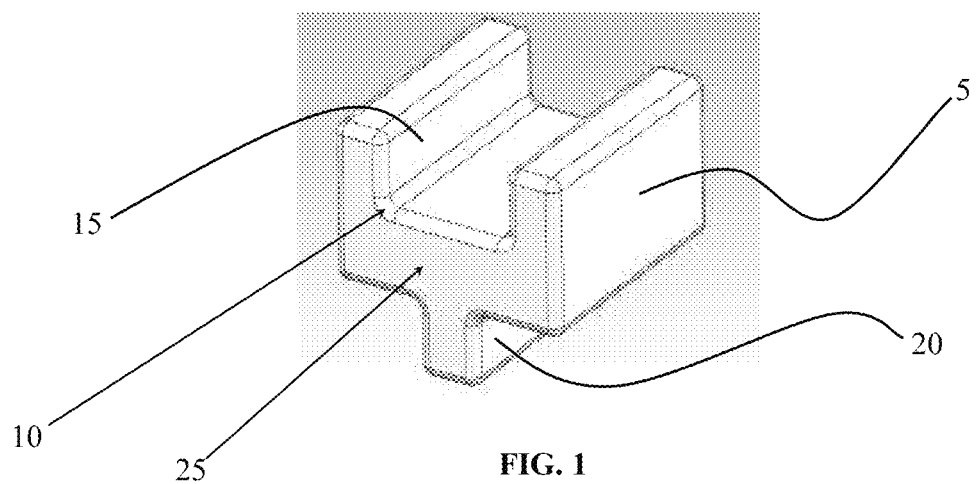
FIG. 1 depicts a perspective view of one embodiment of a Y-shaped "patient-appropriate" blank or template for use with various methods described herein.

A number of significant challenges face the widespread adoption of patient-adapted (e.g., patient-specific and/or patient-engineered) implants and associated surgical procedures, many of which relate to the amount of time required to manufacture the implant, as well as the significant costs associated with creating a unique implant for each individual surgical patient. Unlike standard and/or modular implants, which can be manufactured in bulk and stored for use as needed, patient-adapted implants are generally created after a patient has been identified as a surgical candidate, and the implant is designed and/or selected using imaging data taken of the intended patient's anatomy. The process of designing, manufacturing and finishing the implant can involve a number of steps, typically involving multiple vendors, and this process must result in an acceptable implant before the surgery can occur. In some cases, the creation of a patient-adapted implant from patient imaging data can require more than 4 to 7 weeks, which is a significant delay for both the surgeon and the patient.

An additional challenge facing the acceptance of patient-adapted implants relates to the significant costs associated with creating a unique implant for each individual patient. The unique nature of each patient-adapted implant does not lend their creation to bulk manufacturing methods including high-volume casting techniques. Rather, individual implant components are generally designed and investment cast on an individual basis, or designed and machined from bulk raw materials, which can be a time-consuming and expensive process.

An additional concern relating to the use of patient-adapted implants relates to the availability of processing and manufacturing equipment, as well as the assurance that the implant components will be processed and available for the surgical procedure. Because each patient-adapted implant is unique, and because a significant amount of time and effort is required to create each implant, it is typical practice to manufacture multiple copies (e.g., a primary and a backup implant) of an implant for a single patient, to ensure that at least one implant survives the manufacturing, finishing and testing processes prior to surgical use. However, because such backup implants are only needed where the primary implant has failed, the constant creation of backup implants leads to unused inventory and unnecessary costs where the primary implant does not get damaged. In addition, creating a backup patient-adapted implant often leads to significant wastage where the primary implant is deemed acceptable (which occurs in the vast majority of cases), as the backup implant is generally useless for any other patient and/or procedure and is typically scrapped. Moreover, there are occasions where the primary and back-up implant castings are both damaged, fractured and/or undergo processing missteps that render both implants useless, and there may not be an opportunity to remanufacture another suitable implant within a desired timeframe (or at a desired cost without significant expedited processing fees) for a variety of reasons, which can include a lack of personnel, equipment and/or unavailability of raw materials to create a replacement.

Various embodiments described herein incorporate the use of "blanks" in manufacturing implants. "Blanks," as used herein, refers to a piece of material (e.g., metal, plastic) from which all, or at least a portion, of an implant may be formed through various manufacturing/processing techniques, such as, for example, those techniques discussed below. As described in greater detail below, in some embodiments, a blank may be selected, designed, and/or manufactured with at least a portion that is patient adapted and/or patient appropriate (i.e., appropriate or suitable for forming into a range of differing patient-adapted implants through various manufacturing/processing techniques). Since the piece of material comprising a blank becomes an implant as it transitions through one or more manufacturing/processing techniques, the terms "blank," "implant," and also "casting"

(and combinations and/or variations thereof) are interchangeably used herein to refer to such a piece of material, in the context of any of the various stages during which such a piece of material is being manufactured/processed from a blank to a finished implant, which requires no more processing for use in a surgical procedure.

In some embodiments, blanks may be rapidly manufactured or otherwise modified into suitable patient-adapted implant replacements in the event a primary implant cannot be manufactured in a desired amount of time, at a desired cost, or for various other reasons, including where such primary implants are damaged or fail at various points along the manufacturing process. The capability to create such patient-adapted back-up implants can reduce and/or obviate the need to pre-order multiple copies of an individual patient-adapted implant design to account for failed and/or damaged primary implants. Moreover, even if the blank-manufacturing and/or modification process involves a significant increase in the cost of creating an individual patient-adapted implant (such as, for example, as compared to the cost of manufacturing each individual backup implant copy using standard methods), the overall reduction in implant duplication and wastage may result in significant cost savings.

For example, a femoral implant component may cost approximately $1000 per copy to manufacture using standard casting and machining techniques, with the manufacturing process having a 95% acceptance rate. For 1000 surgeries, this would mean ordering 2000 implants (a primary and a backup implant for each surgery) at a cost of $2 million. At the standard acceptance rate, this would mean that approximately 950 primary implants would be acceptable, with approximately 50 surgeries requiring a backup implant. The unused backup implants would thus constitute 950 backup implants, which were created at a cost of $950,000 (and these implants would now be scrapped). Much of this amount could potentially be saved by using various of the methods and embodiments described herein. For example, the use of blanks and blank-processing methods would obviate the need for the backup implant (at a cost reduction of approximately $1,000,000 for the 1000 backup implants) and, even if the currently disclosed blank manufacturing and modification process cost $5000 per backup implant to accomplish (for a cost of $250,000 for 50 backup implants), an overall savings of $750,000 in manufacturing expense could be realized.

Moreover, in the previous example, a 95% acceptance rate for implants would not only mean that 95% of the primary implants (950 of 1000) would be acceptable, but also that 95% of the backup implants would be acceptable (or that there would be a 5% failure rate for all implants, including the backups). For 50 backup implants, this could mean that at least two (actually a probability estimate of 2.5) of the backup implants would also fail, leaving no implants (primary or backup) available for surgery. In contrast, the use of blanks would allow creation of one or more additional backup implant components, no matter how many failures are encountered, thereby allowing the surgery to move forward as scheduled.

In various embodiments, the described methods can include a comparison or processing step in which, prior to ordering or creating a patient-adapted implant design (such as from a manufacturer and/or 3rd party vendor), the proposed implant design is compared to a selection of one or more blanks (e.g., physical blanks or electronic blank designs) to determine if a backup implant can be created out of an available blank using one or more available manufacturing techniques. If such manufacture is possible, then only a single implant (or whatever number is minimally necessary to accomplish the surgery) is ordered from the vendor/manufacturer. Alternatively, if such manufacture is not possible using a blank (such as where an appropriate blank is on back-order, is not in stock, or is otherwise unavailable; the manufacture cannot be accommodated by a given blank inventory; or the available blank inventory is otherwise undesirable for some reason), then both a primary and backup implant (and, optionally, additional backups, as desired) can be ordered for that specific patient.

In some embodiments, a backup implant may be created from a blank on an as-needed basis or using "just-in-time" manufacturing principles by utilizing precursor patient-adapted or patient-appropriate blanks. Creating patient-adapted blanks may reduce manufacturing time of a backup implant when a fracture, failure or sufficient discrepancy in the manufacturing process requires immediate replacement of the primary implant. The use of blank-manufacturing techniques may also allow expedited production of patient-adapted primary implants, such as, for example, where an implant is needed for emergency surgery to address high-velocity fractures or other trauma, etc.

Patient-adapted blanks may be designed and/or created as patient-appropriate, partially customized, or fully customized. For example, patient-appropriate blanks can include generally standard or generic blanks with a range of shapes and sizes. The size and shape of particular designs of patient-appropriate blanks may be based on features and/or dimensions common to a class of patient-adapted implants that can be formed from the patient-appropriate blanks of the particular design. Various standard, anatomical patient databases or patient image data can be used to select specific features, dimensions, and/or thicknesses to design and/or create specified portions of the patient-appropriate blanks. For example, such specific features/dimensions may include, but are not limited to, anterior/posterior cut distance, intercondylar notch width, presence of integral pegs, position/orientation of pegs, and thickness of implant. Thus, for example, a particular patient-appropriate blank design may have a shape that accommodates formation of integral pegs, and accordingly, the particular design could be appropriate for manufacturing a class of patient-adapted implants that all include integral pegs. Similarly, a particular patient-appropriate blank design may have a size with dimensions that are equal to or larger than corresponding dimensions of a class of patient-adapted implants, and accordingly, the particular design could be appropriate for manufacturing patient-adapted implants of that class. Exemplary embodiments of various blanks that can be patient-appropriate are described in greater detail below. If desired, various designs of patient-adapted blanks may be maintained in inventory, with the most commonly used blanks maintained in higher quantities.

In some embodiments, a patient-adapted blank may be designed and/or created as partially customized or fully customized. For example, one or more features and/or dimensions of a blank may be customized based on information from patient-specific image data.

Blanks may be created by casting, forging, rolling or other processes (including combinations of processes) known in the art. Casting may be performed using standard casting procedures for the blanks. Various forging techniques and methods may be used, such as GFM, closed die forging, firth rixson forging, and/or press forging. Likewise, various rolling processes may be used, such as ring rolling, roll bending, roll forming, profile rolling, and controlled rolling. Depending upon the manufacturing process selected, the patient-adapted blank may have varying material properties and durability. In some embodiments, a forged or wrought material may be desirous, while in others, a cast material may have advantageous qualities.

As discussed above, patient-appropriate blanks of several standard or generic sizes may be available in inventory. Should damage or failure of a patient-adapted implant casting occur during manufacturing process, such as, for example, machining, buffing, or polishing, a patient-adapted blank may be recommended or selected from the available inventory. In some embodiments, software may be configured to utilize a CAD design file created from patient image data to compare the specific dimensions and features of the patient anatomy to the available standard or generic sizes stored in inventory. The software may provide a printout of a recommended size and automatically deduct the size from the inventory database (or may place a "hold" on the blank or other inventory management feature known in the art until acceptance of the finished primary implant is established). Optionally, the software can be programmed to recommend and/or select various alternative options should a recommended size be unavailable, such as, for example, by ordering a backup implant to be casted or machined directly from a wrought ingot, or by choosing an alternative blank design that, although suboptimal in some manner, may be used to create the implant. The software may also identify the time to manufacture, cost and availability to help a technician select the best option to replace the primary patient-adapted implant.

If necessary or desirous, the dimensions and/or material properties of the blank may be considered in altering or otherwise modifying the intended blank design, such as where an increased material strength of the blank allows for a thinner implant, or where a blank of desired dimensions is not available, but an acceptable blank can be manufactured for use which requires alterations to the intended surgical plan and/or surgical tools. In such a case, various features of the blank and/or the comparison process may alter the intended design, surgical procedure and/or tools utilized therein. In a similar manner, an initially chosen (or highly-rated) design for a patient-adapted implant may be altered or rated lower if the intended design has no readily-available blank for creating a backup implant, while an alternate intended design that is "less-acceptable" for one or more reasons (as compared to the other design) does have a blank available for creating a backup.

Various embodiments described herein may utilize patient-adapted blanks stored in inventory to increase the availability and/or accuracy of the manufactured patient-adapted implants. In the event a hospital changes a surgery date scheduled for a patient at the last minute or the patient delays the surgery for any reason, the patient-adapted implant may already be manufactured and stored in inventory or shipped to the hospital for the next scheduled surgery date. Where the surgical date has been significantly extended, or where the patient's anatomy has changed for any reason (e.g., the patient experiences a high velocity knee fracture from a vehicle accident, etc.), the patient joint anatomy may change or may be affected by other external factors. As a result, the patient may require a new implant to be manufactured and the previously manufactured implant to be scrapped. This issue can be resolved by submitting the new patient image data, comparing the patient image data to the available patient-adapted blank inventory, and selecting the appropriate blank to create the new patient-adapted implant. In such a case, the patient may not have to wait an additional 4 to 7 weeks for a new implant to be created.

After recommendation and/or selection of a patient-adapted blank has occurred, a patient-adapted implant can be created from the blank through various manufacturing processes, including, for example by using a 4D or 5D machining process. The 4D or 5D machining process can include the use of multiple processing machines, including multiple software programs and/or machine tool controllers, to machine, for example, in the case of a knee implant, the femoral contact surface and the articulating surface. In various embodiments, the various surfaces of the blank can be machined and/or finished in a single operation or in multiple machining operations.

In various alternative embodiments, blank-specific, implant-specific, and/or patient-adapted fixtures and/or tooling may be designed, selected and/or created to facilitate the manufacturing process. Such a fixture may allow the blank to be attached to multiple milling machines and/or other processing apparatuses without requiring re-registration of the blank with respect to each apparatus. Various embodiments may include designing the blank and/or fixture(s) to connect directly to processing apparatuses (e.g., 4D or 5D mill machine) or to connect by an intermediary, such as, for example, a macro chuck. For example, by attaching the fixture to a macro chuck (with the blank attached to the fixture), the potential for human error and direct technician contact with the implant may be significantly reduced. In various embodiments, a software program may be loaded into an individual machine with patient-specific implant information that facilitates machining and/or further processing of the patient-adapted blank and/or implant.

In various embodiments, once a patient-adapted implant is created from a patient-adapted blank, the implant may undergo additional or further processing. The implant can be buffed, polished and/or cleaned using a variety of standard methods prior to implantation. The implant will then be inspected, packaged and shipped to the appropriate hospital for the scheduled surgery.

In some embodiments, the use of blanks in creating patient-adapted implants can facilitate machining and processing, at least in part, by reducing the amount of material that must milled, drilled, cut and/or otherwise removed from the starting material form. By selecting a blank appropriate to a desired implant size and shape, a desired implant can be created in significantly reduced time, and with significantly reduced effort, as compared to a traditional ingot.

FIG. 1 depicts one embodiment of a Y-shaped patient-appropriate implant blank 5 for use in creating a patient-adapted femoral implant. The body 25 may have varying widths and heights, depending upon the amount of variation in the final patient-adapted design the blank is desired to accommodate. A larger body may be capable of accommodating a larger variation in implant sizes, but will also incorporate a larger amount of material that will typically have to be removed to create a given implant. The height of the body can be designed/selected to incorporate sufficient material to accommodate the formation of various peg heights and/or locations in the implant, or the height can be designed/selected thinner if the use of attachable pegs (e.g., drilled and taped pegs) is contemplated and/or acceptable. The blank may have symmetric medial and/or lateral side walls 15, which can accommodate various orientations (including reversed orientations) of a desired implant design, to accommodate patient anatomy as well as to aid in manufacturing. The blank may have a centered rib 20 on a bottom surface for fixation to a vise, collet or equivalent machine fixation method. In various embodiments, the blank may incorporate radiused edges 10 for various purposes, including ease of machining, for technician handling and/or for casting purposes.

Figure 2:
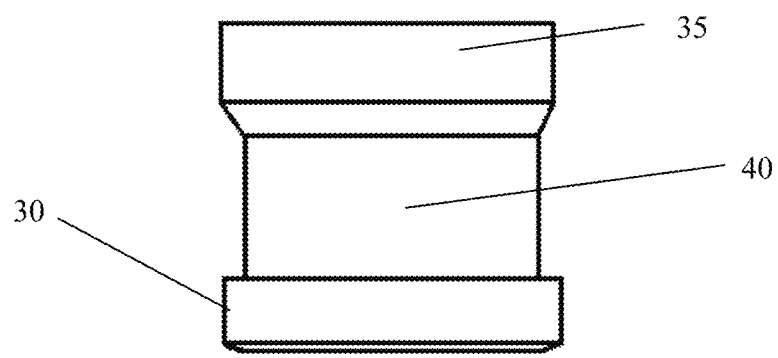
FIG. 2 depicts a top plan view of one alternative embodiment of a Y-shaped blank of FIG. 1.

FIG. 2 depicts the top view of another embodiment of a patient-adapted blank. In this embodiment, a thinner side wall 30 and thicker side wall 35. Side walls with such varying widths may accommodate significant variation in accommodated patient-adapted implant design, as various designs may require, for example, differing material widths for anterior and posterior portions of the implant. For example, depending upon the chosen design, an anterior section of a femoral implant design may require a thicker side wall (e.g., an anterior portion may be thicker or more angled relative to the remainder of the implant), while a posterior portion requires less sidewall thickness. Alternatively, a posterior section of another femoral implant design might require a thicker side wall, while an anterior portion requires less sidewall thickness. Either of the forgoing examples could potentially be accommodated by the blank shown in FIG. 2, with side walls of differing widths. In some embodiments, the thicker side wall 35 could potentially accommodate an implant having condylar portions that accommodate asymmetric bone cuts (e.g., posterior bone cuts separated by a chamfer cut), while the thinner side wall 30 could accommodate a condylar portion for use with a single planar cut. Such side walls of differing thicknesses could, therefore, potentially accommodate a wider range of implant designs than side walls of the same thickness. As previously noted, the bone contacting surface 40 of the blank may be designed with varying widths and lengths to accommodate offset peg locations or large diameter pegs.

Figure 3:
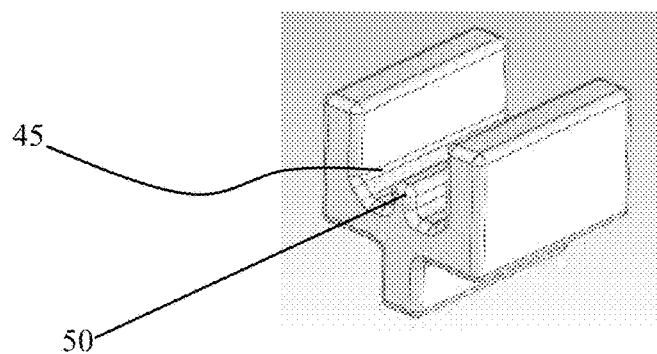
FIG. 3 depicts a perspective view of an embodiment of a W-shaped "patient-appropriate" blank.

FIG. 3 is a perspective view of an embodiment of a W-shaped patient-appropriate blank. The grooves 45 in this blank may include radiused edges to accommodate patient anatomy and/or ease of manufacturability or for various other reasons. Some embodiments can further include a central rail 50, which may be rectangular, square or any other appropriate shape along the length of the implant. In the embodiment shown in FIG. 3, the height of the body is reduced, while the height of the rail 50 allows for machining of one or more anchoring posts for anchoring of the implant to the underlying bony anatomy.

Figure 4:
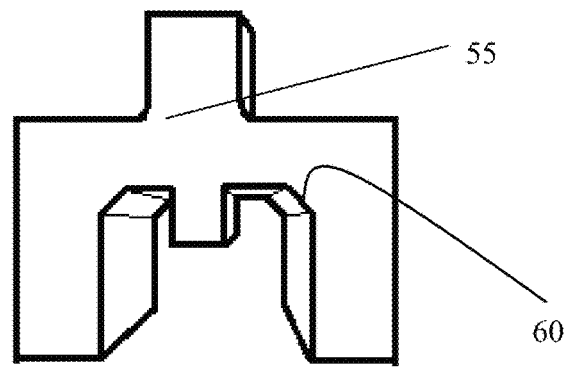
FIG. 4 depicts a side view of the W-shaped blank of FIG. 3.

FIG. 4 is a front view of a W-shaped blank embodiment. A central rib 55 can be used to mate, connect or otherwise attach the blank to a vise or other processing machinery. The rib 55 can be designed with varying widths or heights to accommodate different types of vises and/or commercially-available machining equipment. In some embodiments, the grooves may also be designed with chamfers 60 instead of radiused or square edges.

Figure 5:
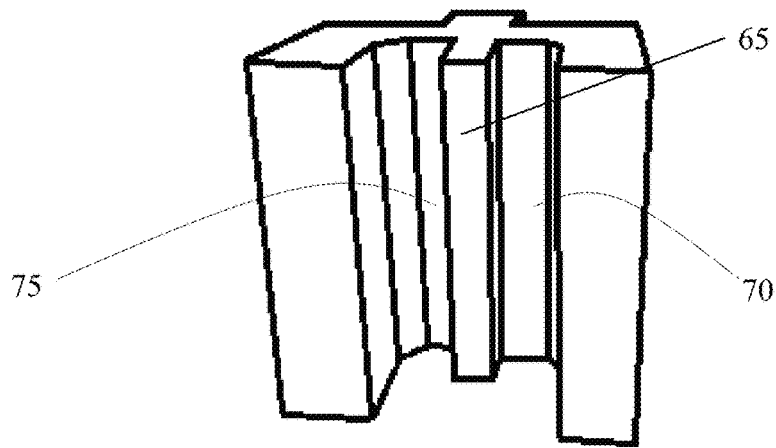
FIG. 5 depicts the top view of the W-shaped blank of FIG. 3.

FIG. 5 is a top view of a W-shaped blank embodiment. Rail 65 may be designed with a variety of thicknesses to accommodate larger diameter pegs or offset pegs. In some embodiments, the rail 65 does not run continuous throughout the length of the blank. For example, in some embodiments, the rail 65 may be configured as two separate rails, leaving a flat surface in the center. The rail 65 may also be designed to be offset, such as, for example, with the medial groove 75 and the lateral groove 70 having differing widths and/or heights.

Figure 6:
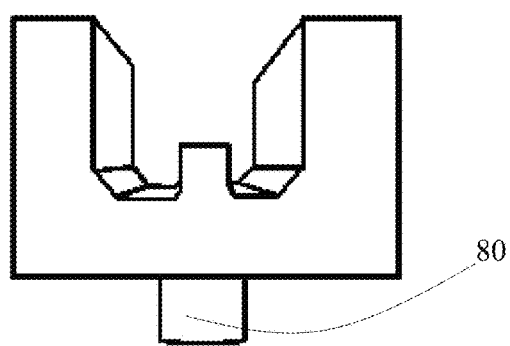
FIG. 6 depicts an alternate side view of the W-shaped blank of FIG. 3.

FIG. 6 depicts a side view of a W-shaped blank having a cylindrical rod 80, which can be configured to attach to a variety of collet sizes and/or shapes for a mill machine or other machines that require and/or utilize collets for attachment purposes. Similarly, some embodiments may include a Y-shaped blank having a similar connection cylinder.

Figure 7:
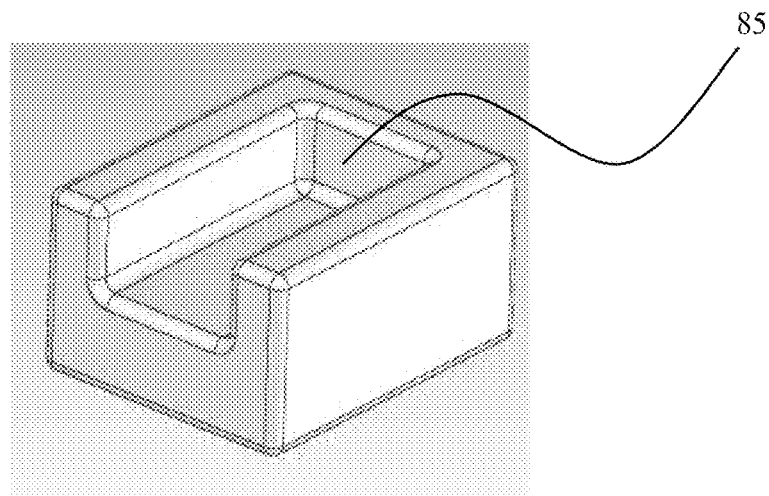
FIG. 7 depicts one embodiment of a U-shaped blank having a backing plate adapted for tool fixturing.

FIG. 7 depicts a perspective view of a patient-appropriate blank incorporating a backing plate 85 to accommodate connection to tool fixtures. The backing plate may be used to attach to variety of mechanisms for machining purposes or other machines for further processing.

Figure 8:
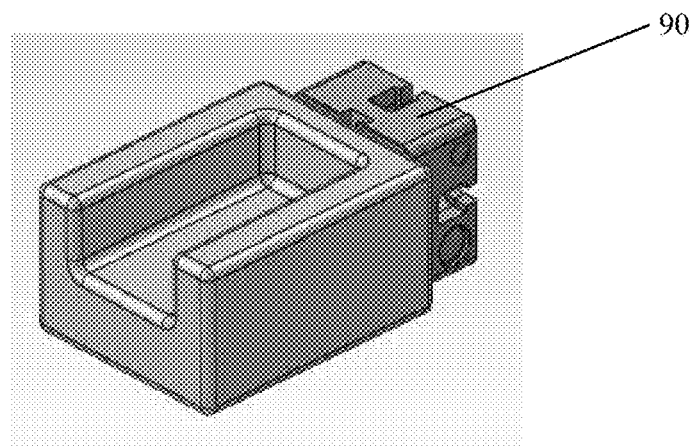
FIG. 8 depicts a perspective view of the U-shaped blank of FIG. 7 with an attached 3R macro chuck.

FIG. 8 depicts a perspective view of the patient-appropriate blank and backing plate of FIG. 7 attached to a 3R macro chuck 90. The macro chuck may be attached to the appropriate milling machine to stabilize the blank while undergoing the implant machining process.

Figure 9:
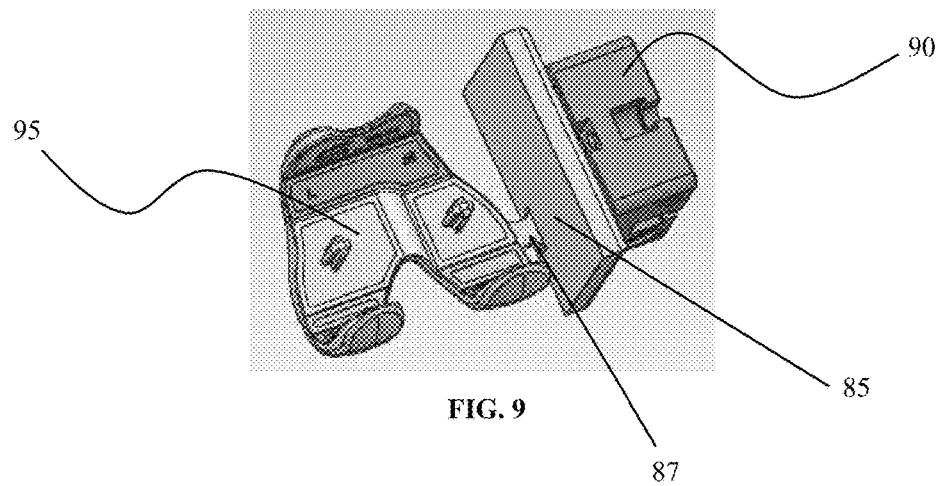
FIG. 9 depicts a perspective view of one embodiment of a patient-adapted implant machined out of the U-shaped blank of FIG. 8.

FIG. 9 depicts a perspective view of an embodiment of a patient-adapted implant 93 created from the patient-appropriate blank of FIG. 8. In this embodiment, the 3R macro chuck 90 is secured to the backing plate 85 to rigidly secure the blank during the machining of the patient-adapted implant 93. The patient-adapted implant may desirably remain attached to the backing plate 85 by one or more connections or tabs 87, which can be subsequently removed from the backing plate 85 by mechanical means, such as cutting, sawing, bending, etc. In various embodiments, the connections can be located on outer articulating and/or sidewall faces of the implant, although virtually any location on the implant consistent with the present disclosure can be utilized.

Various embodiments described herein include the use of patient-adapted fixtures during various portions of manufacturing/processing. In various embodiments, at least a portion of the blank has been machined or otherwise processed to create one or more patient-adapted surfaces on the implant, while some remaining portion of the blank has not been machined or processed into a final patient-adapted shape. This remaining portion may include some or all of a portion of the blank that connects the machined portion to the machining and/or processing apparatuses already used. In various embodiments, a patient-adapted fixture, which corresponds to one or more of the patient-adapted surfaces (e.g., surfaces already machined) of the blank, can be engaged and attached to the blank at the corresponding location(s), connection(s) to any machining/processing apparatus can be released or otherwise severed or removed, and the blank can be secured by the fixture while some or all of the remainder of the blank is machined and/or otherwise processed to complete the production of the patient-adapted implant (including portions that were connected to any machining/processing apparatus). The patient-adapted fixture can include known dimensions, sizes and/or orientations for itself, as well as the blank it secures, and this information can be utilized by subsequent machinery, measuring and/or processing equipment in further machining, processing, finishing and/or inspection of the patient-adapted implant.

Figure 10:
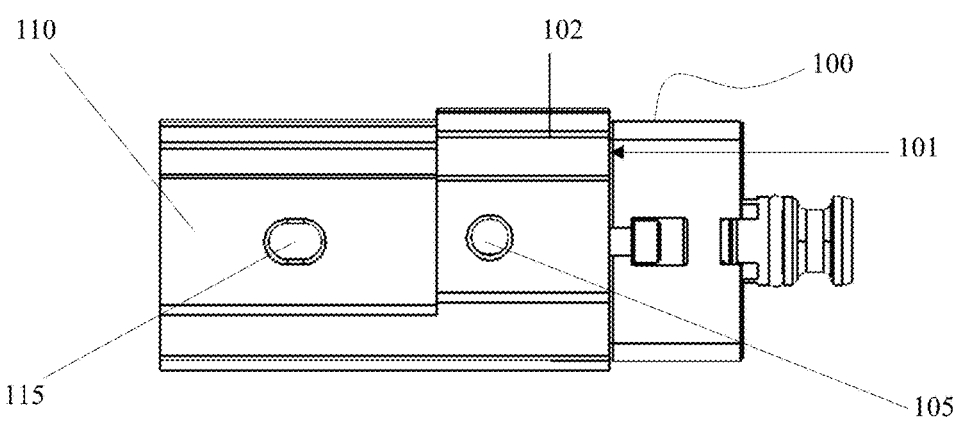
FIG. 10 depicts the top view of one embodiment of a patient-adapted fixture.

In one embodiment, shown in FIG. 9, a blank has been machined such that a bone-facing surface 95 of the patient-adapted implant 93 is in a final form for implantation and, optionally, much of the articulating surface of the implant has been initially machined. At least a portion of a connection tab 87 of the implant remains connected to the backing plate 85 of the blank. In addition much of the articulating surface (not shown) will require additional smoothing, processing and/or polishing prior to implantation. FIG. 10 depicts a top view of a patient-adapted fixture 103 created to hold and secure the patient-adapted implant of FIG. 9 for further processing (e.g., machining, milling, cutting, warping, drilling, smoothing, shaping, finishing, buffing, polishing, cleaning, inspecting, drag finishing). In some embodiments, the fixture can include a plurality of holes (two, in the figure) that may be of equal or unequal diameters, shapes and/or alignments to accommodate one or more pegs of the patient-adapted blank/implant. A first hole 105 can be designed to have a fixed location and/or orientation on the fixture relative to a connection device 100, which may be configured to be secured to connecting surface of fixture 103. This fixed location can allow the CAD design file and/or the automated machinery to calibrate a starting position and/or implant location and/or orientation for initiation of the machining process. In some embodiments, the fixture can include a first datum edge 102, a second datum edge 101 and/or an axial position concentric with the first hole 105.

In various alternative embodiments, the first hole 105 may be the same or of a smaller or larger diameter than the second hole 115. The second hole 115 may be designed to have varying locations based on the specific patient's anatomy. The location of the second hole may be different for each patient-adapted implant. Also, the second hole 115 may be designed to have a larger diameter than the first hole 105 to accommodate small diameter adjustments, variances and/or inaccuracies of the distance between the two pegs. The mating surface 110 may be designed to seat the bone contacting surface of the patient-adapted implant. The mating surface 110 may have a flat mating surface or it may be angled for the best fit. Moreover, the holes may be designed to extend completely through the height of the fixture and tapered to fit a small collet.

Figure 10A:
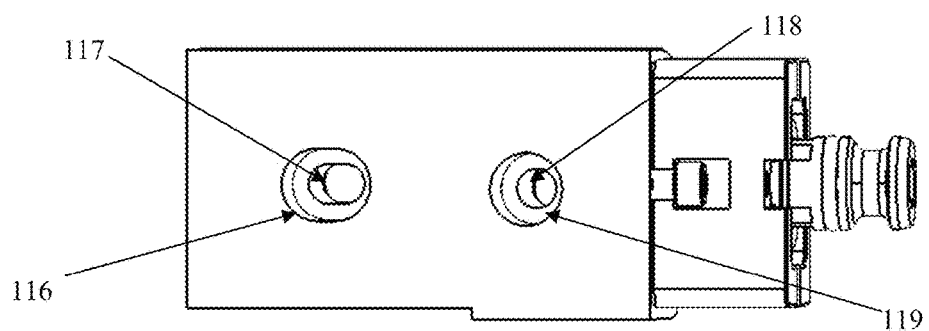
FIG. 10A depicts a bottom view of the patient-adapted fixture of FIG. 10.

FIG. 10A depicts a close-up top view of another embodiment of a patient-adapted fixture. The figure illustrates a first reduced diameter hole 118 in a first hole 119 on the mating surface, and second reduced diameter hole 117 in a second hole 116 on the mating surface. In some embodiments, the reduced diameter holes 118, 117 may be designed with a step-down diameter reduction rather than a tapered hole. This step-down diameter reduction from second hole 116 on the mating surface to the second reduced diameter hole 117 can allow a collet assembly to have a positive stop or provide positive feedback to the technician to stop retracting the collet assembly further. The shelf on the collet can be retracted slowly when placed concentrically in the first 119 and second 116 hole until the collet assembly stops. This may ease manufacturing procedures by eliminating a need for constant measuring and reducing potential damage to the implant.

Figure 11:
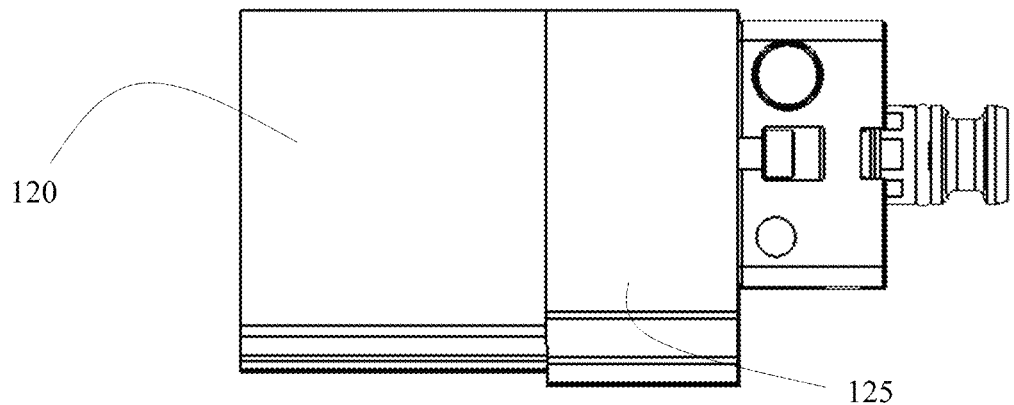
FIG. 11 depicts a side view of the patient-adapted fixture of FIG. 10.

FIG. 11 depicts the side view of one patient-adapted fixture embodiment incorporating medial and lateral placement surfaces. The medial placement surface 125 and lateral placement surface 120 are surfaces desirably formed to be patient-adapted and correspond to the inner, bone-facing surfaces of the patient-adapted surfaces already created on a blank. In the embodiment shown in FIG. 11, the placement surfaces are of different heights and slightly offset, which corresponds to the slightly offset bone-contacting surfaces of the implant. When the posts of the patient-adapted implant are placed into the first and second holes (see FIG. 15), a pair of collets that can be slid over the posts can be tightened and secure the implant to the fixture in a known manner. In this embodiment, the holes and placements are specifically designed and positioned to ensure that the implant cannot be secured to the fixture in a reverse orientation (i.e., the implant cannot be secured to the fixture in both a forward and 180 degree reverse orientation), thereby eliminating manufacturing errors due to misaligning the implant backwards on the fixture. The fixture desirable secures the implant in a known position/orientation relative to a connector 100 secured to the fixture.

Figure 12:
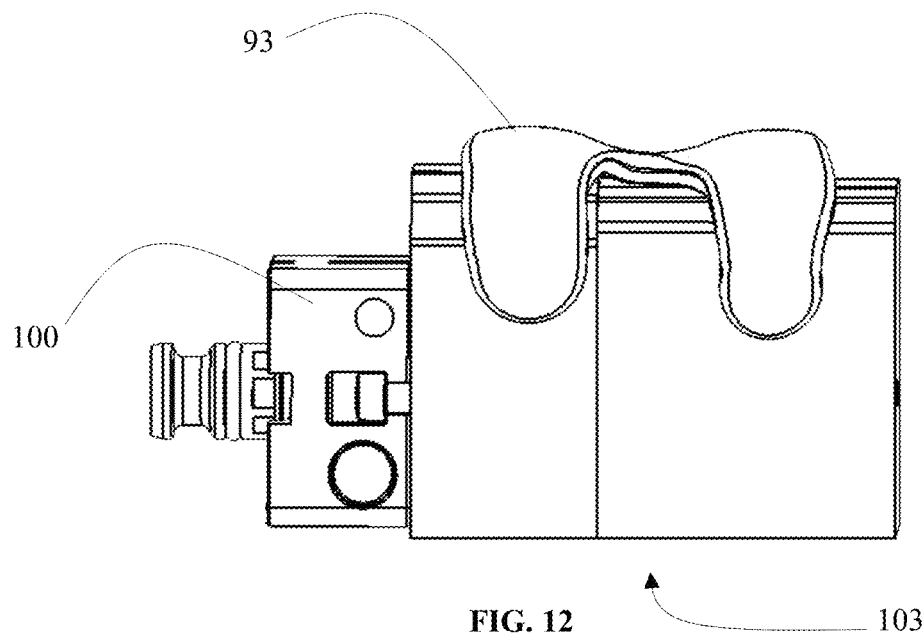
FIG. 12 depicts a side view of a patient-adapted fixture and implant.
Figure 13:
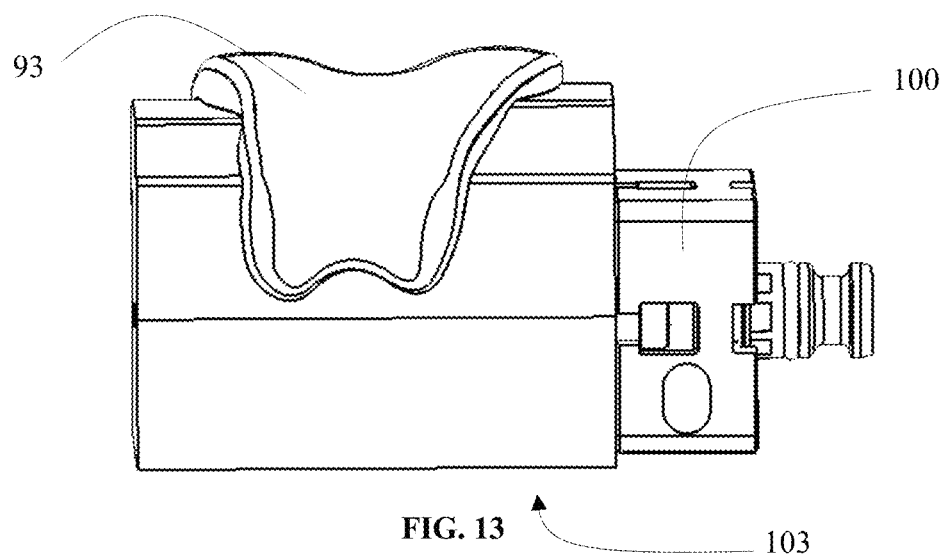
FIG. 13 depicts an opposing side view of the patient-adapted fixture and implant of FIG. 12.
Figure 14:
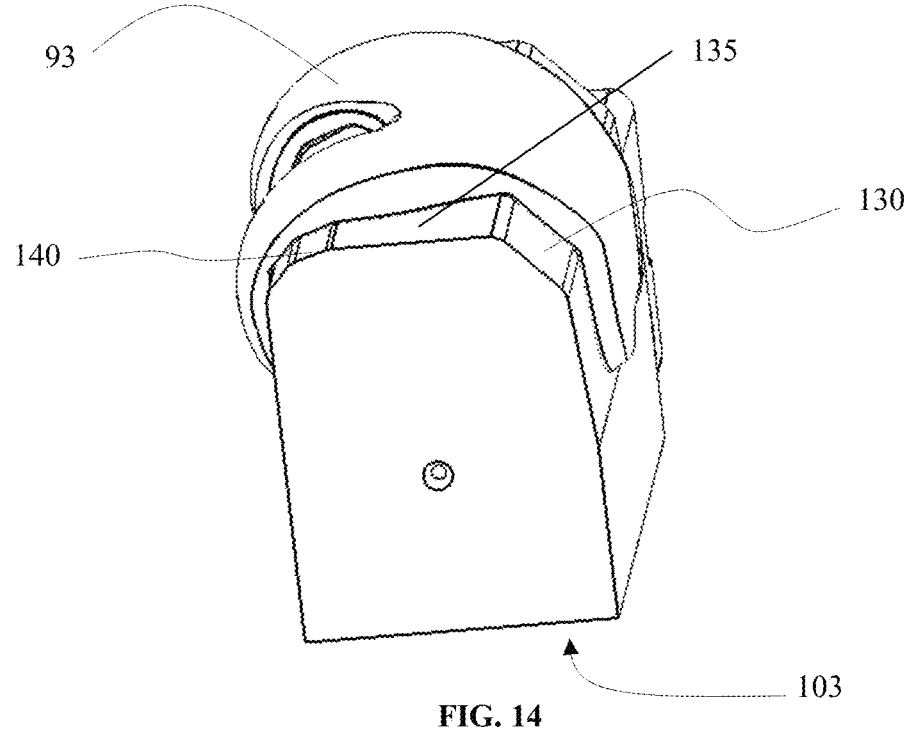
FIG. 14 depicts a side view or "end-on" view of the patient-adapted fixture and implant of FIG. 12.

FIGS. 12, 13, and 14 depict a patient-adapted implant 93 seated on the patient-adapted fixture 103, with the bone-facing surfaces of the implant being desirably flush with the medial and lateral placement surfaces. As previously noted, the posts of the implant are desirably inserted into the first and second holes of the fixture, and the implant is secured to the fixture via collets, which secures the implant in a known orientation and position relative to the fixture. In turn, the fixture is secured to a connector 100 (e.g., a chuck) for further attachment to one or more processing apparatuses. Because the location and orientation of the connector 100 is known relative to the fixture, and the location and orientation of the fixture is known relative to the implant, the processing apparatus can be programmed with the desired patient-adapted implant shape file, and can utilize various processing methods (e.g., machining, milling, cutting, warping, drilling, smoothing, shaping, finishing, buffing, polishing, cleaning, inspecting, drag finishing) to prepare the articulating surface of the implant. Moreover, the connector 100 may be released from one machine, and moved to another, with the known relationship between the connector, fixture and implant allowing subsequent equipment to process the patient-adapted implant without requiring additional "set-up" time.

If desired, the fixture may have first 140 and second 130 edges that are chamfered (as shown in FIG. 14) or radiused edges and that may accurately fit the implant. In some embodiments both first 140 and second 130 edges may be symmetrical in dimensions, while in other embodiments they may also be designed to have different angles or widths to mimic the resection cuts from the bone contacting surface of the patient-adapted implant. As previously mentioned, the mating surface 135 may be flat or have a specified angle to accommodate the bone contacting surface of the implant.

Figure 15:
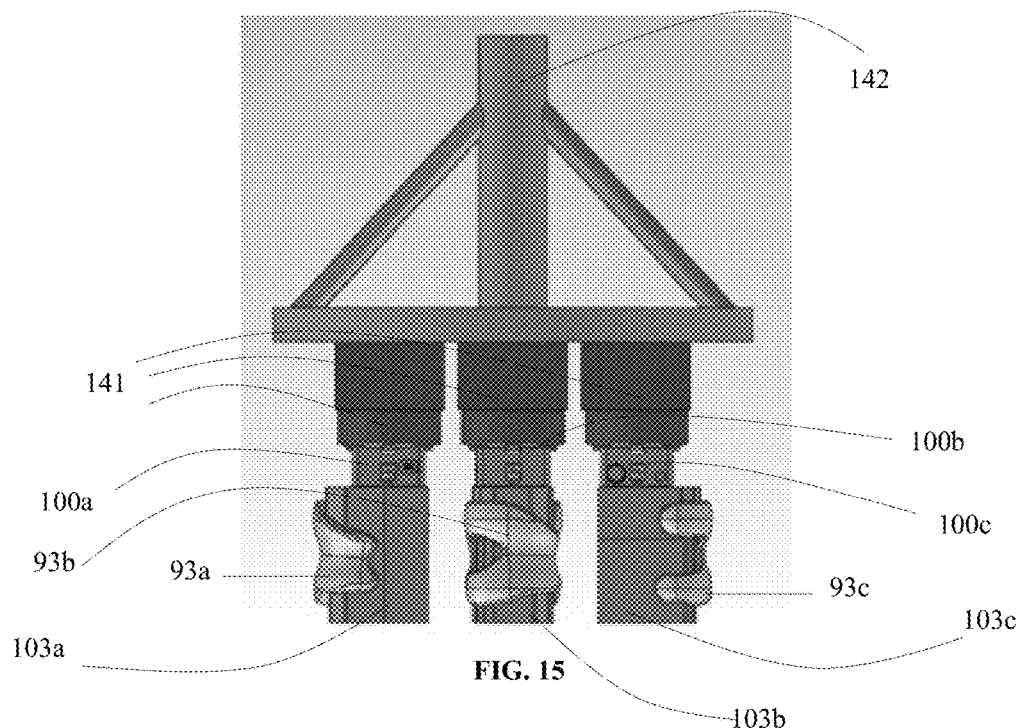
FIG. 15 depicts a perspective view of patient-adapted implants and fixtures connected to a drag-finishing apparatus.
Figure 16:
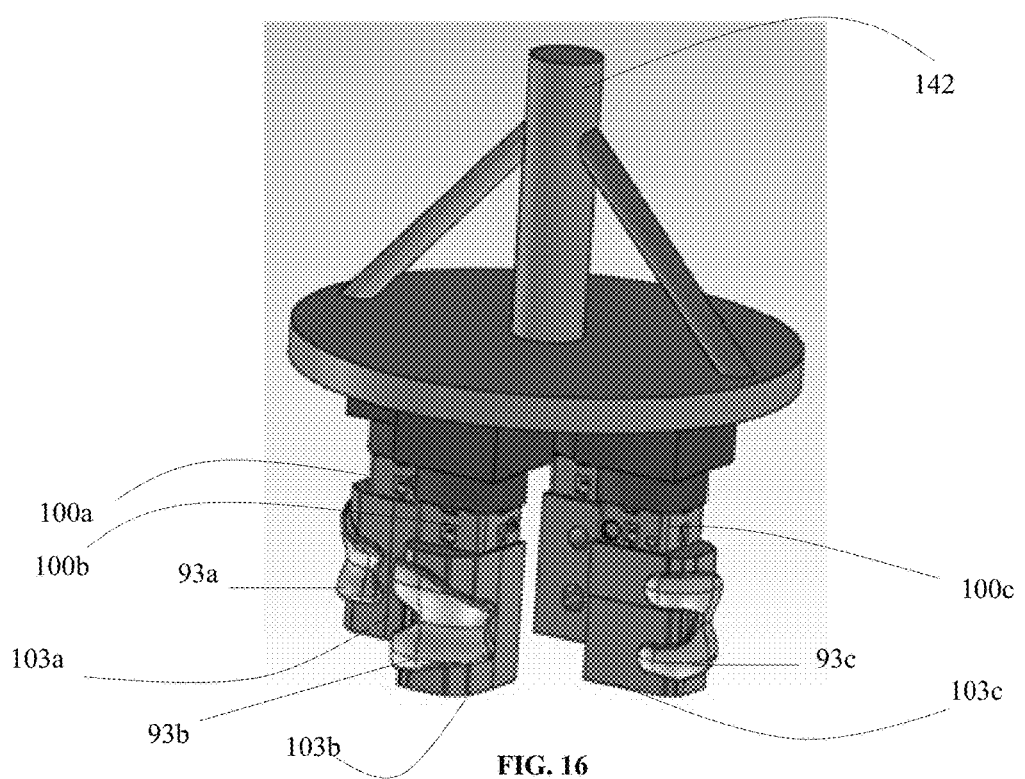
FIG. 16 depicts a perspective view of patient-adapted implants and fixtures connected to a drag-finishing apparatus.

As discussed above, in some embodiments, patient-adapted fixture 103 may facilitate securing patient-adapted implant 93 in various processing apparatuses. A drag finishing machine can be one example of such a processing apparatus. For example, as shown in FIGS. 15 and 16, one or more patient-adapted implants 93*a-c* may each be secured to a patient-adapted fixture 103*a-c*, respectively, and each of the patient-adapted fixtures 103*a-c* may be connected via connectors 100 to spindles 141 of a drag-finishing drive unit 142. In such a configuration, the drag finishing drive unit 142 may then be controlled to drag the patient-adapted implants 93*a-c* through a bed of mass finishing media. In some embodiments, the drag-finishing drive unit may be rotated, and likewise, each of the spindles 141 may be rotated and/or rotate the respective patient adapted fixtures 103*a-c*. In some embodiments, the engagement surfaces of the patient-adapted fixtures 103*a-c* may abut substantially the entirety of the bone-facing surfaces of the respective patient-adapted implants 93*a-c*. In this manner, all or nearly all of the bone-facing surfaces of the patient-adapted implants 93*a-c* would be covered and prevented from coming into contact with the bed of mass finishing media during the drag-finishing process, and thus, only side and joint-facing (articulating) surfaces of the patient-adapted implants 93*a-c* would be processed by the drag-finishing. Drag finishing may be used for, for example, surface grinding, deburring, edge breaking and radiusing, and/or surface smoothing (e.g., smoothing an articulating surface of an implant).

Figure 17:
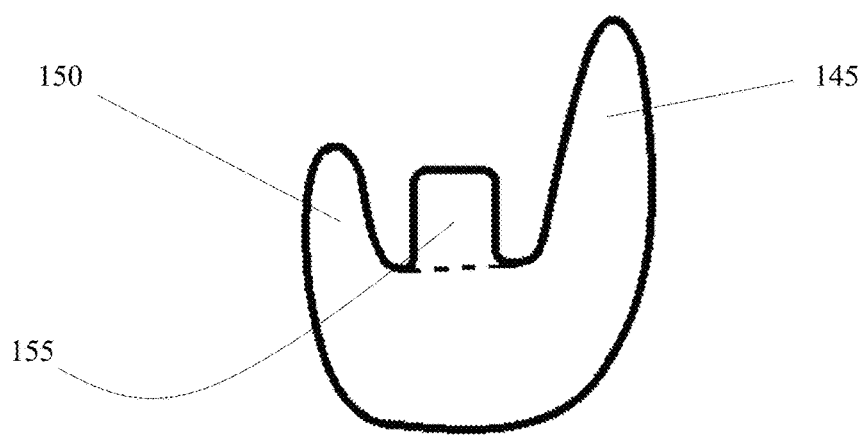
FIG. 17 depicts a cross-sectional view of one embodiment of an asymmetric "W" shaped blank.

FIG. 17 depicts a cross-sectional view of one embodiment of an asymmetric W-shaped blank. This blank may be created by rolling, casting or forging, and can also be formed out of an elongated wrought ingot. The first side 145 of the asymmetric embodiment may be designed to have a longer or taller height than the second side 150. The first and second sides may have any type of edge that will accommodate further machining, including, for example, radiused, beveled or flat edges. The asymmetric blank may also have a rail 155 to assist with the machining of the pegs. The rail 155 may be of various widths and/or heights to accommodate the changing anatomy of the patients. The rail 155 may also be removed to have an asymmetric "U" shaped embodiment.

Figure 18:
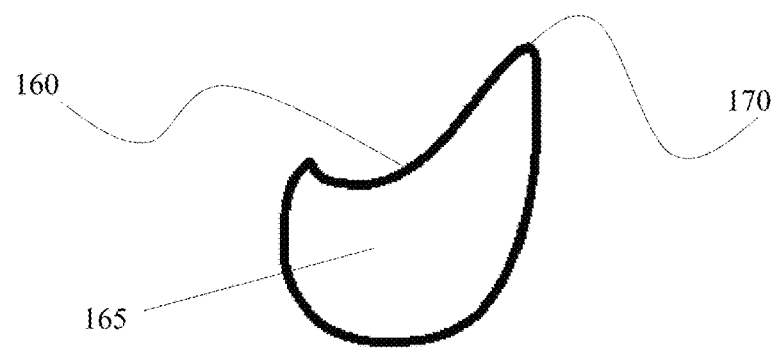
FIG. 18 depicts a cross-sectional view of an asymmetric "moon" shaped blank.

FIG. 18 depicts a front view of a "moon" shaped blank embodiment. This asymmetric blank may be created by rolling, casting or forging. Also, the device manufacturer may also consider to make this asymmetric profile of a wrought ingot. The bone-facing surface 160 may have different concavity dimensions. The width 165 may also vary with the patient anatomy. The first side 170 may be designed to a different height with radiused edges.

Figure 19:
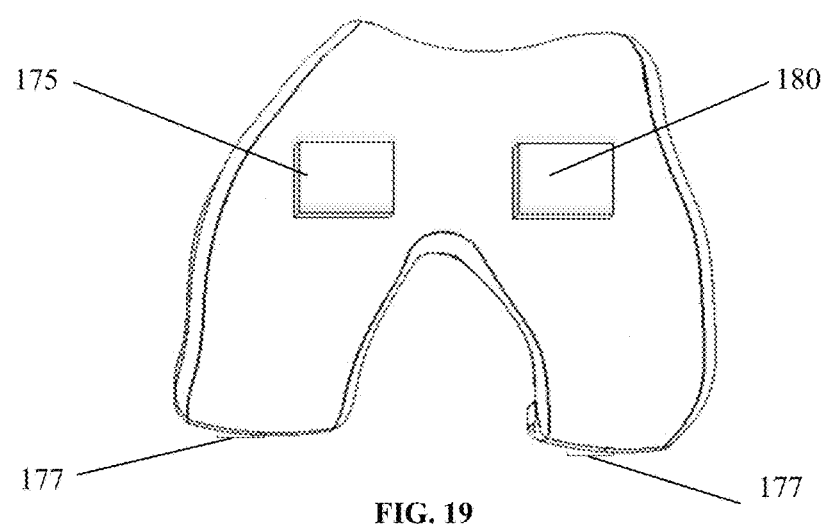
FIG. 19 depicts a view of an unfinished articulating surface of a patient-adapted implant casting.

FIG. 19 depicts the articulating surface view of one embodiment of a patient-adapted implant, which may be created as part of a primary implant order. This casting can include a patient-adapted bone-facing surface (not shown) with a joint-facing surface of the implant that may require some additional machining and/or processing, including, for example, the removal of gates 180 and 180 and/or vent holes 177 from the implant. The casting may undergo a variety of processes to remove the gates, including removal by milling, machining, buffing, and/or polishing. Further processing for the articulating surface can include milling, machining, buffing, drag-finishing, and/or polishing of the articulating surface (as well as, optionally, any additional surfaces) to desired shapes, sizes, thicknesses and/or surface finishes. In various embodiments, a patient-adapted fixture can be utilized with, for example, the implant of FIG. 19 to accomplish various processing steps, including the removal of cast gates, vents and/or connections (or other remaining unnecessary and/or unwanted materials and/or artifacts on an implant and/or implant blank), and processing of unfinished surfaces of the implant. For example, where the bone-facing surface of the implant requires little or no additional processing, a patient-adapted fixture appropriate to the bone-facing surfaces can be designed and/or selected, and the implant secured to the fixture. The implant, which will have a known location and orientation relative to the fixture (which in turn can have a known location and orientation relative to some other reference point, such as an attached collet or chuck) can then be connected, directly or indirectly (e.g., by means of one or more intermediary connectors) to various processing apparatuses, which may, for example, incorporate software and/or patient-specific data suitable, for further processing of the implant, including machining, milling, cutting, warping, drilling, smoothing, shaping, finishing, buffing, polishing, cleaning, inspecting, drag finishing, etc. If desired, the fixture can be moved between various machines and/or measuring instruments, with the known relationship between the fixture and the implant service to quickly register the implant location/orientation relative to the programmed patient-specific data.

Figure 20:
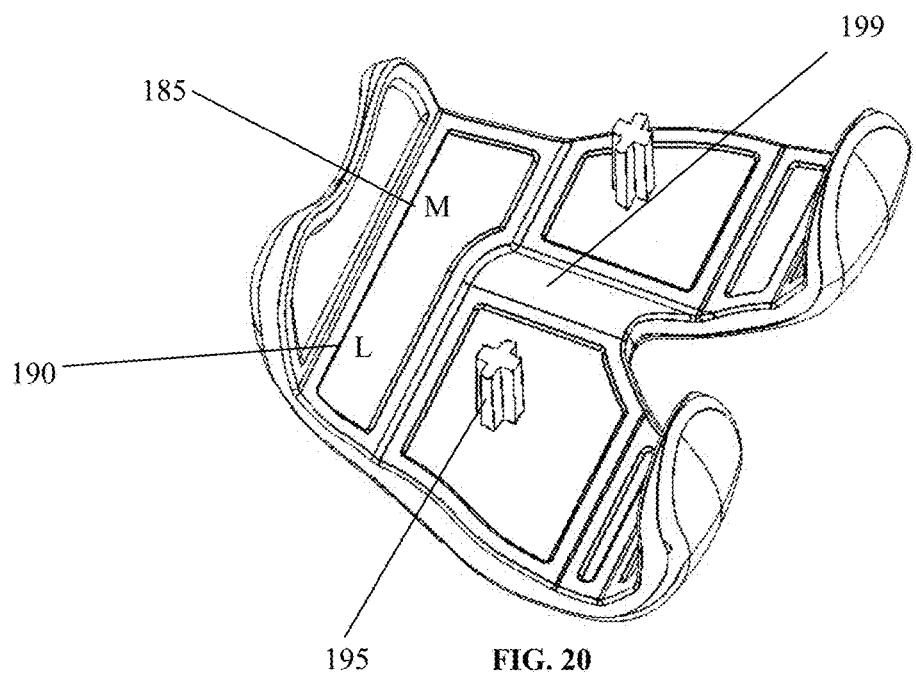
FIG. 20 depicts various bone contacting surfaces of the patient-adapted implant casting of FIG. 19.

FIG. 20 depicts the bone-facing surface of an unfinished patient-adapted implant. The implant includes medial and lateral side indicia 185 and 190, which desirably simplifies placement of the implant on the fixtures and ensures accurate alignment. In this embodiment, the pegs 195 and bone-facing surfaces are unfinished and/or porous to desirably increase attachment to the underlying bone surface. The pegs 195 may be shaped in a "cross" or "plus" design to facilitate cement interdigitation through the small channels of the pegs 195. The pegs 195 may be designed into the forged, rolled or casted blank, or may be separate structures secured to the implant at a later time by drilling and tapping the hole for a screw thread attachment.

Figure 21:
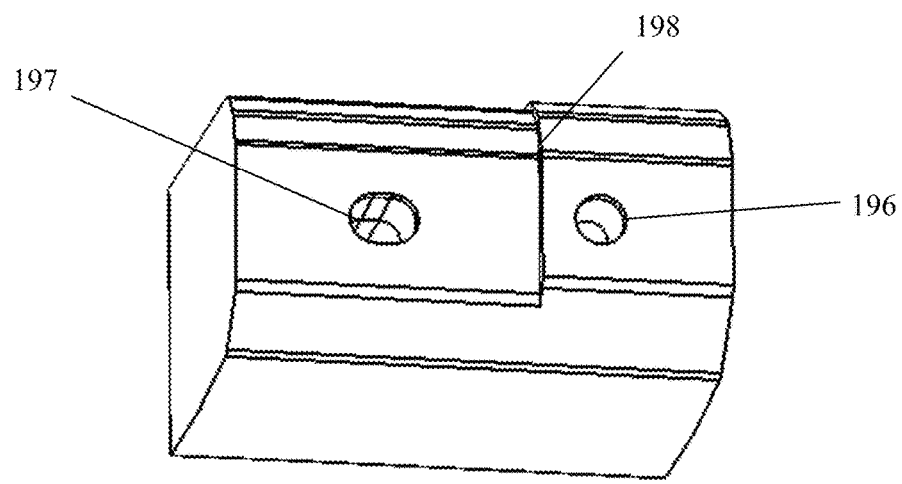
FIG. 21 depicts a top view of a machined aluminum "patient-appropriate" fixture.

FIG. 21 depicts an embodiment of a patient-adapted fixture, which may be constructed out of a metallic material such as, for example, aluminum or brass. This embodiment includes a first hole 196 and a second hole 197 for engaging the implant (such as the implant shown in FIG. 20) to the fixture. The engagement (i.e., implant-contacting) surfaces of the fixture can correspond to various bone-facing surfaces of a patient-adapted implant requiring further processing as described herein. The fixture can further include one or more step cuts 198 between adjacent medial and lateral surfaces that can accommodate implants having different height distal cuts on medial and lateral bone-facing surfaces. In various embodiments, the implant-contacting surfaces of the fixture can correspond to some portion, or optionally all, of the bone-facing surfaces of the implant. For example, the fixture of FIG. 21 incorporates two upper surfaces separated by a vertical step cut 198. However, the inner surfaces of the implant of FIG. 20 includes two inner surfaces separated by an angled or tapered step cut 199, which does not precisely correspond to the vertical step cut 198 of the fixture. Yet, the fixture may still adequately accommodate the implant of FIG. 20, even though the entirety of the surface of the fixture is not patient-adapted.

In some embodiments, engagement surfaces of the fixture may be used to assess the fit of the bone-facing surfaces of the blank. For example, the engagement surfaces of the fixture may be engaged (e.g., placed in contact) with the bone-facing surfaces of the implant blank, to determine if the bone-facing surfaces have been completely and properly machined and/or otherwise processed. If the fit is poor, and the fixture cannot be placed in sufficient contact with bone-facing surfaces of the implant blank, this fact may indicate that the bone-facing surface of the implant blank has not yet been completely and properly machined and/or otherwise processed. Because the implant blank has not yet been separated or otherwise detached from the equipment, the equipment can be utilized to continue the machining process. Moreover, if the machine or cutting tools have failed or worn to unacceptable levels, the failure/worn tools can be repaired and/or replaced, and the processing of the implant blanks finished and assessed again. Once confirmation has been obtained, the partially-machined implant blank may be removed from processing equipment and/or any connections (such as, for example, connections to the backing plate) can be separated. Optionally, the implant blank may then be connected to the same or a different patient-adapted fixture and further processed, as described herein.

Figure 24:
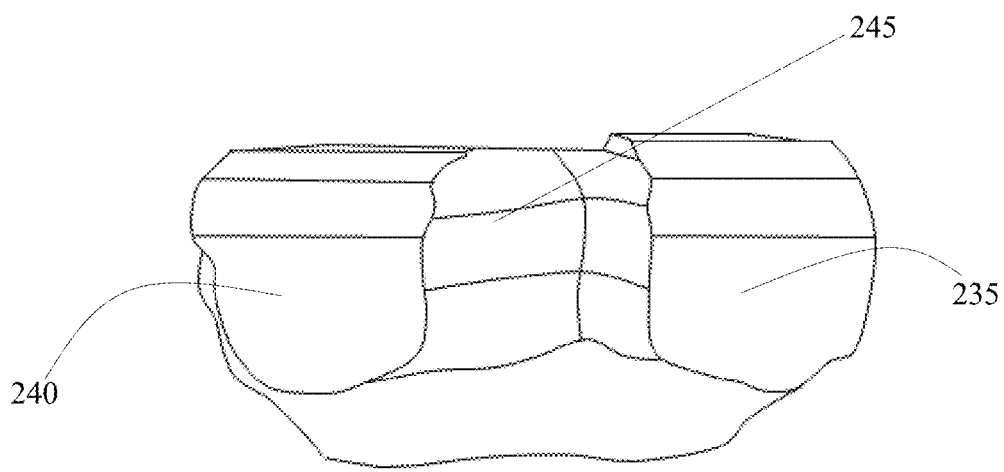
FIG. 24 depicts the top view of a patient-adapted femoral bone fixture.

FIG. 24 depicts a top view of a patient-adapted femoral bone fixture incorporating proposed medial 235 and lateral 240 condylar resection cuts. A femoral bone fixture may be created and/or designed to be fully or partially patient-adapted, and the outer surfaces of the fixture can reflect one or more of the intended surgical resection cuts, the intended inner bone-facing surfaces of the implant and/or varying combinations thereof. If desired, the image data gathered from each patient to create the CAD design file can be used to create the femoral bone fixtures, or data defining the inner surfaces of the implant can be used. For example, in the embodiment shown in FIG. 24, the patient image data was used to provide the dimensions of the medial 235 condyle resected cuts, the lateral 240 condyle resected cuts, and the condylar notch 245 width. In some embodiments, the femoral bone fixture may be created using three-dimensional polymer printing techniques, or other three-dimensional printing techniques known in the art, or can be machined out of various materials using standard techniques. Similarly, the CAD design file with the patient-specific image data can be sent to a 3rd party vendor to manufacture the femoral bone fixtures using standard ULA process, plastics or a variety of metals.

In various embodiments, the femoral bone fixture may comprise a patient-adapted fixture for securing the implant blank for further processing, as described herein. Similarly, a patient-adapted fixture may comprise a femoral bone fixture which verifies that desired machining (and/or other processing steps) have been completed on various blank surfaces prior to removal and/or detachment from machining equipment.

Figure 22:
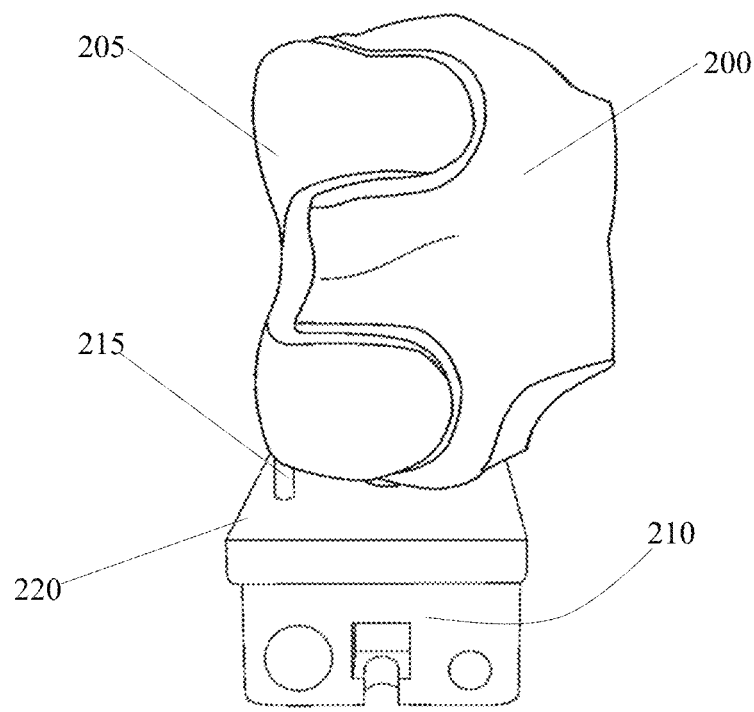
FIG. 22 depicts the front view of a patient-adapted femoral bone fixture docked with a partially-machined patient-adapted implant attached to a macro chuck.

FIG. 22 depicts a front view of a patient-adapted femoral bone fixture 200 positioned in contact with a machined patient-adapted implant 205 attached to a macro chuck 210 via post 215. In this embodiment, the manufacturer may use the patient-adapted femoral bone fixture 200 to assess the bone-facing surface of the patient-adapted implant 205 prior to removing the implant from the macro chuck 210. Such inspection may require the manufacturer to pause or stop the 4D or 5D mill machine after it has machined the bone-facing surface of the patient-adapted implant 205 or wait until the mill machine has completely finished machining the implant. The manufacturer can attempt to align the femoral bone fixture 200 within the bone contacting surface of the implant 205 to ensure that dimensions are accurate. If the manufacturer has difficulty aligning the femoral bone fixture 200 with the implant 205, this fact may indicate a need for further inspection of the implant, equipment and/or the femoral bone fixture.

Alternatively, the implant 205 may require adjustment of the CAD design file or other changes/alterations to accommodate the femoral bone fixture 200. The mill machine will make the dimensional adjustments to the implant 205 and the manufacturer may re-inspect with the femoral bone fixture 200. This process may be repeated in an iterative fashion, until the implant 205 passes the inspection. Once the implant 205 passes inspection, the patient-adapted implant 205 may be detached from the face plate 220 by removing the material tab 215 (e.g., by cutting, sawing, bending, and/or machining the tab 215 off).

Figure 23:
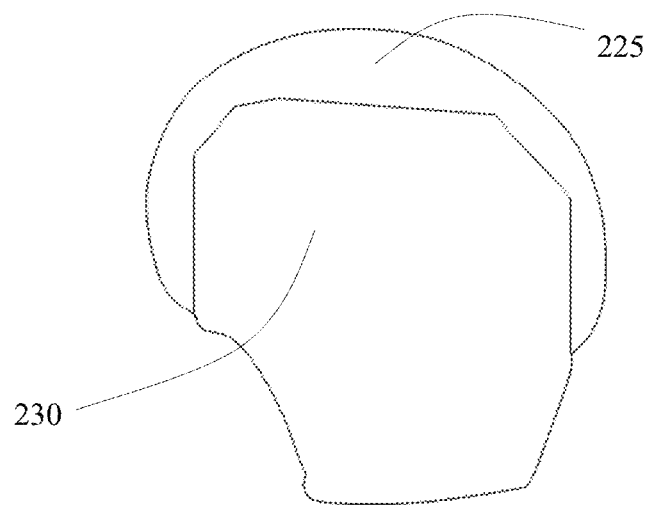
FIG. 23 depicts a side view of the patient-adapted femoral bone fixture showing one ideal fit of the patient-adapted implant.

FIG. 23 depicts a side view of an ideal fit and alignment of a patient-adapted femoral bone fixture 230 with a patient-adapted implant 225. In some embodiments, after the manufacturer detaches the implant 225 from the face plate 230, the implant may undergo further processing (e.g., machining, milling, cutting, warping, drilling, smoothing, shaping, finishing, buffing, polishing, cleaning, inspecting, drag finishing). The femoral bone fixture 230 may be used again after the further processing to ensure that the further processing did not affect the dimensions of the patient-adapted implant 225.

Figure 25:
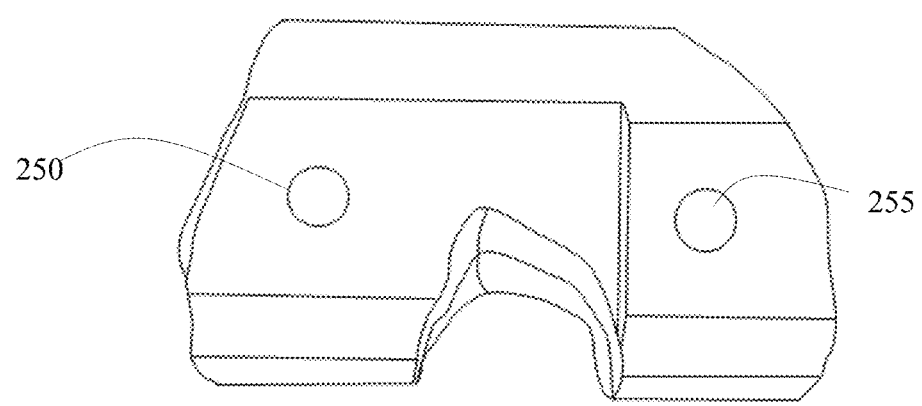
FIG. 25 depicts the bottom view of FIG. 24 showing the collet insertion holes.

FIG. 25 depicts the bottom view of a patient-adapted femoral bone fixture showing medial and lateral holes 255 and 250. The manufacture may decide to create or design the femoral bone fixture to be "free-floating," or the fixture can attach to the bone-facing surfaces of the implant using a collet or other assembly. The manufacturer may then decide to conduct further processing on the implant supported on the femoral bone fixture.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A fixture for use in manufacturing a surgical implant for treating a portion of a bone of a patient, the fixture comprising:
   an outer surface, the outer surface including:
      an engagement portion configured to engage a patient-specific portion of the implant in a known orientation during at least a portion of the manufacturing of the implant; and
      a connecting portion, the connecting portion configured for releasably connecting to one or more processing apparatuses in a predetermined orientation,
   wherein the engagement portion includes first and second holes, the first and second holes sized and positioned to accommodate first and second pegs, respectively, extending from the implant when the implant is engaged with the engagement portion in the known orientation.

2. The fixture of claim 1, wherein the engagement portion of the outer surface of the fixture substantially matches one or more planned bone-cut surfaces of the portion of the bone of the patient.

3. The fixture of claim 1, wherein the portion of the implant comprises one or more bone-facing surfaces of the implant.

4. The fixture of claim 3, wherein the engagement portion of the outer surface of the fixture substantially mirrors the one or more bone-facing surfaces of the implant.

5. The fixture of claim 1, wherein the connecting portion is configured to be secured in a predetermined orientation to a connector for connecting to the one or more processing apparatuses.

6. The fixture of claim 1, wherein the connector is a chuck.

7. A set of fixtures for use in manufacturing patient-specific knee implants, the set of fixtures comprising:
   a first fixture for use in manufacturing a first implant for treating a portion of a femur of a first patient, the first fixture comprising:
      an outer surface, the outer surface including:
         an engagement portion configured to engage a patient-specific_portion of the first implant in a known orientation during at least a portion of the manufacturing of the first implant; and
         a connecting portion, the connecting portion configured for releasably connecting to one or more processing apparatuses in a predetermined orientation,
      wherein the engagement portion includes:
         a first hole sized to accommodate a first peg extending from the first implant, the first hole located in a standard, fixed location relative to the connecting portion; and
         a second hole sized to accommodate a second peg extending from the first implant, the second hole located in a patient-specific location based on the location of the second peg relative to the first peg of the first implant; and
   a second fixture for use in manufacturing a second implant for treating a portion of a femur of a second patient, the second fixture comprising:

an outer surface, the outer surface including:
an engagement portion configured to engage a patient-specific_portion of the second implant in a known orientation during at least a portion of the manufacturing of the second implant; and
a connecting portion, the connecting portion configured for releasably connecting to one or more processing apparatuses in a predetermined orientation,
wherein the engagement portion includes:
a first hole sized to accommodate a first peg extending from the second implant, the first hole located in the standard, fixed location relative to the connecting portion; and
a second hole sized to accommodate a second peg extending from the second implant, the second hole located in a patient-specific location based on the location of the second peg relative to the first peg of the second implant,
wherein the first and second hole of the first fixture are separated by a distance that is not equal to the distance separating the first and second hole of the second fixture.

\* \* \* \* \*